(12) United States Patent
Prentice

(10) Patent No.: US 7,569,362 B2
(45) Date of Patent: Aug. 4, 2009

(54) METHODS AND CONSTRUCTS FOR EXPRESSING POLYPEPTIDE MULTIMERS IN EUKARYOTIC CELLS USING ALTERNATIVE SPLICING

(75) Inventor: Holly Prentice, Carlisle, MA (US)

(73) Assignee: Biogen Idec MA Inc., Cambridge, MA (US)

(*) Notice: Subject to any disclaimer, the term of this patent is extended or adjusted under 35 U.S.C. 154(b) by 41 days.

(21) Appl. No.: 11/079,933

(22) Filed: Mar. 15, 2005

(65) Prior Publication Data
US 2005/0221430 A1 Oct. 6, 2005

Related U.S. Application Data

(60) Provisional application No. 60/553,478, filed on Mar. 15, 2004.

(51) Int. Cl.
C12P 21/06 (2006.01)
C12N 5/06 (2006.01)
C12N 15/85 (2006.01)
C07H 21/04 (2006.01)

(52) U.S. Cl. ............... 435/69.1; 435/325; 435/455; 530/350; 536/23.5

(58) Field of Classification Search ............... 435/69.1, 435/325, 455; 530/350; 536/23.5
See application file for complete search history.

(56) References Cited

U.S. PATENT DOCUMENTS

| | | | | |
|---|---|---|---|---|
| 5,043,270 | A | * | 8/1991 | Abrams et al. ............. 435/69.1 |
| 5,561,053 | A | * | 10/1996 | Crowley .................... 435/69.1 |
| 6,228,360 | B1 | * | 5/2001 | Co et al. .................. 424/145.1 |
| 6,613,328 | B2 | | 9/2003 | Co et al. |
| 2005/0019925 | A1 | | 1/2005 | Krummen et al. |

OTHER PUBLICATIONS

Helfman et al Molecular and Cellular Biology, 1986, 3582-3595.*
Ngo et al., 1994, The protein Folding Problem and Tertiary Structure Prediction, pp. 491-495.*
Breitbart et al Annual Review of Biochemistry, 1987, 56, 467-495.*
Andreadis et al Nucleic acid research, 1995, 23, 3585-3593.*
Pergolizzi, et al. C. R. Biologies, 2004, 327: 695-709.*
Thomas et al. Nature Rev.Genet. 2003, 4: 346-358.*
Verma et al Annu Rev Biochem. 2005;74:711-38.*
Sun et al (Mol Cell Biol. 2000; 20(17): 6414-6425.*
Manson, et al. Genomics, 2001, 77(3): 127-34.*
New England Bio Lab catalogue: BstBI.*
Brem, H., et al., "Interstitial chemotherapy with drug polymer implants for the treatment of recurrent gliomas," *J. Neurosurg.* 74:441-446, American Association of Neurological Surgeons (1991).
Chabot, B., "Directing alternative splicing: cast and scenarios," *TIG* 12:472-478, Elsevier Science Ltd. (1996).
Eck, S.L. and Wilson, J.M., "Gene-Based Therapy" in *Goodman & Gilman's The Phamacological Basis of Therapeutics, 9th Ed.*, Hardman, J.G., and Limbird, L.E., eds., McGraw-Hill, New York, pp. 77-101 (1996).
Deonarain, M.P., "Ligand-targeted receptor-mediated vectors for gene delivery," *Exp. Opin. Ther. Patents* 8:53-69, Ashley Publications Ltd. (1998).
Hanes, J., et al., "New advances in microsphere-based single-dose vaccines," *Adv. Drug Del. Rev.* 28:97-119, Elsevier Science B.V. (1997).
Langer, R., "New Methods of Drug Delivery," *Science* 249:1527-1533, American Association for the Advancement of Science (1990).
Lucas, B.K., "High-level production of recombinant proteins in CHO cells using a dicistronic DHFR intron expression vector," *Nucl. Acids. Res.* 24:1774-1779, Oxford University Press (1996).
"Mammalian Expression Vectors: Introduction of Vectors into Host Cells," in *Vectors A Survey of Molecular Cloning Vectors and Their Uses*, Rodriquez, R.L. and Denhardt, D.T., eds., Butterworth Publishers, Stoneham, MA, pp. 470-472 (1988).
Urlaub, G., et al., "Deletion of the Diploid Dihydrofolate Reductase Locus from Cultured Mammalian Cells," *Cell* 33:405-412, MIT (1983).
Yang, N.-S., Gene Transfer into Mammalian Somatic Cells In Vivo, *Crit. Rev. Biotechnol.* 12:335-356, CRC Press, Inc. (1992).
International Search Report for International Application No. PCT/US05/08473, United States Patent and Trademark Office, Alexandria, Virginia, mailed Nov. 15, 2005.
Norderhaug, L., et al., "Versatile vectors for transient and stable expression of recombinant antibody molecules in mammalian cells," *J. Immunol. Methods* 204:77-87, Elsevier Science B.V. (1997).
Thanaraj, T.A. and Clark, F., "Human GC-AG alternative intron isoforms with weak donor sites show enhanced consensus at acceptor exon positions," *Nucleic Acids Res.* 29:2581-2593, Oxford University Press(2001).
Zhu, Y., et al., "Multigene lentriviral vectors based on differential splicing and translational control," *Mol. Ther.* 4:375-382, Academic Press (2001).

* cited by examiner

*Primary Examiner*—Valarie Bertoglio
*Assistant Examiner*—Anoop Singh
(74) *Attorney, Agent, or Firm*—Sterne, Kessler, Goldstein & Fox P.L.L.C.

(57) ABSTRACT

The invention provides a method of producing multiple polypeptides, such as antibodies or antibody fragments, in a eukaryotic cell using a single expression vector. The expression vector is engineered to comprise two or more expression cassettes under the control of a single promoter wherein the expression cassettes have splice sites which allow for their alternative splicing and expression as two or more independent gene products at a desired ratio. Use of the vector for the efficient expression of recombinant antibodies in eukaryotic host cells is disclosed as well as the use of such antibodies in diagnostic and therapeutic applications.

33 Claims, 4 Drawing Sheets

Fig. 4

Exemplary Splice Sites

| | | vector | seq. identifier |
|---|---|---|---|
| Swa I | BstB I | | |
| intron | exon | | |
| aaatctgcag\|TCTT\|CGAACAGG | | pHLP005 | (SEQ ID NO: 1) |
| tttagacgtc\|AGAAG\|CTTGTCC | | | (SEQ ID NO: 2) |
| aattctgcag\|TCACCGTCCTT | | pHLP006 | (SEQ ID NO: 3) |
| ttaagacgtg\|AGTGGCAGGAAGC | | | (SEQ ID NO: 4) |
| aattctgcac\|TCACCGTCCTT | | pHLP007 | (SEQ ID NO: 5) |
| ttaagacgtg\|AGTGGCAGGAAGC | | | (SEQ ID NO: 6) |
| aattgtgcag\|TCACCGTCCTT | | pHLP010 | (SEQ ID NO: 7) |
| ttaacacgtc\|AGTGGCAGGAAGC | | | (SEQ ID NO: 8) |
| aattctgcaa\|TCACCGTCCTT | | pHLP011 | (SEQ ID NO: 9) |
| ttaagacgtt\|AGTGGCAGGAAGC | | | (SEQ ID NO: 10) |
| aagctagcag\|TCACCGTCCTT | | pHLP012 | (SEQ ID NO: 11) |
| ttcgatcgtc\|AGTGGCAGGAAGC | | | (SEQ ID NO: 12) |
| aattctgcgg\|TCACCGTCCTT | | pHLP013 | (SEQ ID NO: 13) |
| ttaagacgcc\|AGTGGCAGGAAGC | | | (SEQ ID NO: 14) |
| aagaggcctc\|TCACCGTCCTT | | pHLP014 | (SEQ ID NO: 15) |
| ttctccggag\|AGTGGCAGGAAGC | | | (SEQ ID NO: 16) |
| aaggggggcag\|TCACCGTCCTT | | pHLP015 | (SEQ ID NO: 17) |
| ttccccccgtc\|AGTGGCAGGAAGC | | | (SEQ ID NO: 18) |
| aagctagcag\|TCGACCACCTT | | pHLP016 | (SEQ ID NO: 19) |
| ttcgatcgtc\|AGCTGGTGGAAGC | | | (SEQ ID NO: 20) |
| ccggagggggcag\|TCACCGTCCTT | | pHLP017 | (SEQ ID NO: 21) |
| tccccccgtc\|AGTGGCAGGAAGC | | | (SEQ ID NO: 22) |
| atggggggggcag\|TCACCGTCCTT | | pHLP018 | (SEQ ID NO: 23) |
| ttgtaccccccgtc\|AGTGGCAGGAAGC | | | (SEQ ID NO: 24) |
| ccggattctgcag\|TCACCGTCCTT | | pHLP019 | (SEQ ID NO: 25) |
| taagacgtc\|AGTGGCAGGAAGC | | | (SEQ ID NO: 26) |
| atggttctgcag\|TCACCGTCCTT | | pHLP020 | (SEQ ID NO: 27) |
| ttgtaccaagacgtc\|AGTGGCAGGAAGC | | | (SEQ ID NO: 28) |

METHODS AND CONSTRUCTS FOR EXPRESSING POLYPEPTIDE MULTIMERS IN EUKARYOTIC CELLS USING ALTERNATIVE SPLICING

CROSS REFERENCE TO RELATED APPLICATIONS

This application claims the benefit of U.S. Provisional Application No. 60/553,478, filed Mar. 15, 2004, which is herein incorporated by reference in its entirety.

BACKGROUND OF THE INVENTION

1. Field of the Invention

Certain embodiments of the invention disclosed herein relates to vectors and methods for expressing polypeptide multimers in eukaryotic cells, both in vitro and in vivo, using alternative splicing. Methods for producing cells containing these vectors are included, as well as the use of these vectors and the polypeptides expressed therefrom for the treatment of disease and for the efficient in vivo or in vitro production of such multimeric proteins.

2. Description of Background and Related Art

Polypeptide multimers are assemblies of two or more polypeptides that together form a complex. The polypeptides that make up the complex are usually different. Antibodies are a typical polypeptide multimer in that they are comprised of two antibody light chain polypeptides and two antibody heavy chain polypeptides which together form a tetrameric complex.

The expression of polypeptide multimers in host cells is a challenging process in that the expression of each different polypeptide that makes up the polypeptide multimer must be carefully coordinated. For example, to express an antibody in eukaryotic cells, a first gene encoding the antibody light chain and a second gene encoding an antibody heavy chain must be introduced into the cell and expressed within an acceptable range of ratios. Expression of an unacceptable ratio of antibody light to heavy chain within the same cell or culture system may result in a highly inefficient production of the desired multimeric complex or in cell or organismal toxicity.

Past approaches for expressing polypeptide multimers in eukaryotic cells include introducing two or more vectors, each vector separately encoding each of the different polypeptides that make up the polypeptide multimer. Each vector typically carries a promoter driving expression of one polypeptide of the complex, and at least one vector typically encodes a selection marker. The vectors are then, in series or together, introduced into a cell (usually by transfection) and the cells are co-selected for the expression of both selection markers.

In another approach, a coding sequence along with a promoter for each polypeptide making up the polypeptide complex, is engineered into a single vector. This approach eliminates the need for working with multiple vectors, but still does not eliminate the potential for promoter competition between each coding sequence. Also, this approach can not typically resolve the problem of expressing the individual polypeptides comprising the protein multimer in an acceptable ratio to result in efficient expression of the protein multimer.

Thus, in either of the above approaches, a consistent ratio of the two products may not always be obtained in the host cell. This can be due to factors such as differential promoter activity, promoter competition for cellular factors required for optimal expression, efficiency of transcription and/or translation of the protein multimer component polypeptides, and/or a difference in the copy number for each of the vectors introduced into the cell.

Splicing vectors utitlizing a single splice donor and splice acceptor have also been developed. U.S. Pat. No. 5,043,270 discloses a minigene expressing a selectable marker, e.g. DHFR, and has an intron that contains a gene encoding a protein of interest. U.S. Pat. No. 5,561,053 discloses the inverse situation, in which the gene encoding a protein of interest contains an intron 5' to the coding sequence. This intron contains a gene encoding a selectable marker bounded by the splice donor and acceptor. This type of intronic expression vector is further described in Lukas, B. K., et al. *Nucleic Acids Res.* 24:1774-1779 (1996). U.S. Pat. Appl. Pub. No. 2005/0019925 A1 discloses similar intronic vectors with a fusion selectable marker. It also discloses the use of two pairs of splice donors and splice acceptors for the expression of more than one protein of interest. All of these published constructs, however, rely on pairs of splice donors and splice acceptors, i.e., have one splice donor matched to a single splice acceptor. Each of these constructs depends on highly efficient splicing at all sites for effectiveness. There is no reference to using a single splice donor to activate alternative splicing from more than one splice acceptor to express multiple polypeptides. Further, there is no suggestion of the desirability of expressing the polypeptides at different ratios, or the substitution of different splicing acceptors to control the relative expression of the polypeptides.

Accordingly, a need exists for a construct that links the expression of two or more genes in a consistent ratio, such that the resultant gene products are efficiently produced and assembled.

SUMMARY OF THE INVENTION

The invention solves the foregoing problems of expressing a polypeptide multimer in a host cell using one expression vector by linking the expression of two or more genes through the use of alternative splicing. Accordingly, a single vector having one promoter can be used to drive the expression of a pre-mRNA that can be spliced into two or more different mRNA transcripts such that the two or more mRNA transcripts encode different polypeptides. Thus, the relative expression of the two or more products is not influenced by differential activity of independent promoters, promoter competition, or vector copy number.

In particular, the invention provides a method for introducing a single expression vector into a eukaryotic cell using a single promoter to drive the transcription of a single pre-mRNA that is then alternatively spliced into two or more different gene products which can then be translated into two or more different polypeptides. In one embodiment, the gene products encode the polypeptide subunits of a multimeric protein. In a further embodiment, the gene products are antibody light and heavy chains that comprise an antibody.

Accordingly, the invention has several advantages which include, but are not limited to, the following:
 providing a vector for expressing multiple polypeptides, in particular, heteromeric polypeptides such as antibodies or antibody fragments;
 an efficient method of producing multiple polypeptides, for example, antibody heavy and light chain polypeptides, in a eukaryotic cell such as an animal cell or a yeast cell;
 an efficient method of producing recombinant antibodies for use in diagnostic or therapeutic applications; and
 recombinant antibodies produced by the method, for treating a subject in need of a recombinant antibody therapy.

Accordingly, in one embodiment, the invention provides an expression vector comprising, in a 5' to 3' or downstream direction, a promoter, e.g., the CMV promoter; a 5' untranslated region (UTR) providing, e.g., a capping signal; a splice donor; an intron; a first splice acceptor; a first exon encoding a first polypeptide; a second splice acceptor; and a second exon encoding a second polypeptide, wherein the promoter is operably linked to the first and second exon. Splice sites (i.e., donors and acceptors) can be naturally occurring splice sites, engineered splice sites, for example, synthetic splice sites, canonical or consensus splice sites, or non-canonical splice sites, e.g., cryptic splice sites. Each exon can further comprise a polyadenylation signal.

Here, the term "first" or "second" as applied to a genetic element such as an exon, intron, any splice site, etc., is used merely to identify and distinguish various elements from one another and does not refer to the actual linear placement or numbering of elements within a gene or to the order in which pre-mRNA molecules encoding separate polypeptide components of a protein multimer are expressed.

In another embodiment, the vector contains one splice donor and more than one splice acceptor, for example, two, three, four, five, six, seven, eight, nine, ten or more splice acceptors. Each splice acceptor is associated with an exon located just downstream of the splice acceptor. Therefore, the vector contains more than one exon, for example, two, three, four, five, six, seven, eight, nine, ten or more exons.

In one embodiment, the first polypeptide is the heavy chain of an antibody and the second polypeptide is the light chain of the antibody or, alternatively, the first polypeptide is the light chain of an antibody and the second polypeptide is the heavy chain of the antibody.

In a related embodiment, the light and/or heavy chain is murine, chimeric, humanized, or human. The light or heavy chains can contain amino acid alternations such as the introduction or ablation of glycosylation sites in, e.g., the Fc region.

In another embodiment, the first and second polypeptides are expressed in a ratio of about 20:1 to about 1:20, about 15:1 to about 1:15, about 12:1 to about 1:12, about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2, or about 1:1. In particular embodiments, the first and second polypeptides are expressed in a ratio of about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19 and/or about 1:20. The determination of the ratio is typically determined using art recognized techniques such as reverse transcriptase polymerase chain reaction (RT-PCR) or Northern blots (for measuring the relative amounts of transcripts) or immunoblot or enzyme linked immunosorbent assay (ELISA) techniques (for measuring relative amounts of polypeptides).

In one embodiment, the vector comprises SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, or 28.

In a related embodiment, the vector comprises SEQ ID NO: 29.

In another embodiment, the invention provides a eukaryotic cell containing the foregoing vector capable of expressing two or more alternatively spliced gene products.

In one embodiment, the alternative splicing vector of the present invention is integrated into the chromosomal DNA of the cell, and in yet another embodiment, the vector is episomal. In related embodiments, the alternative splicing cassette or construct of the present invention is integrated into the chromosomal DNA of the cell. In another related embodiment, the alternative splicing cassette or construct of the present invention is episomal. In still other related embodiments, the alternative splicing vector of the present invention comprises a viral vector.

In another embodiment, the eukaryotic cell containing the vector of the invention is a mammalian cell, such as, for example, a baby hamster kidney cell, a fibroblast, a myeloma cell, an NS0 cell, a PER.C6 cell, or CHO cell, or, alternatively, an insect cell, such as, for example, a *Spodoptera frugiperda* (Sf9) cell, a *Tricoplusia ni* (Tn. TnHigh-Five) cell, or a *Bombyx mori* (BMN) cell. Alternatively, the eukaryotic cell containing the vector of the invention is a yeast cell, for example a *Saccharomyces* cell, *Schizosaccharomyces* cell, or a *Pichia* cell.

In another embodiment, the invention provides a method of producing polypeptides, the method comprising culturing the foregoing cell containing the alternative splicing vector or expression cassette or construct of the present invention followed by isolating the first and second polypeptides from the cell culture.

In one embodiment of the method, the first and second polypeptides form a polypeptide multimer such as an antibody.

In another embodiment, the invention provides the foregoing peptide multimer, produced by the method, for the manufacture of a medicament for treatment or prevention of a disease or disorder.

In another embodiment, the invention provides for the delivery of the alternative splicing vector or the alternative splicing cassette or construct to a patient in vivo.

In a further embodiment, the invention provides for the delivery of the alternative splicing vector or the alternative splicing cassette or construct to a patient's cells or tissue ex vivo. In related embodiments, the present invention also provides return of the patient's cells or tissues comprising the alternative splicing vector or the alternative splicing cassette or construct to the patient's body.

Other features and advantages of the invention will be apparent to one of ordinary skill in the art from the following detailed description and claims.

BRIEF DESCRIPTION OF THE DRAWINGS/FIGURES

Figure 3:
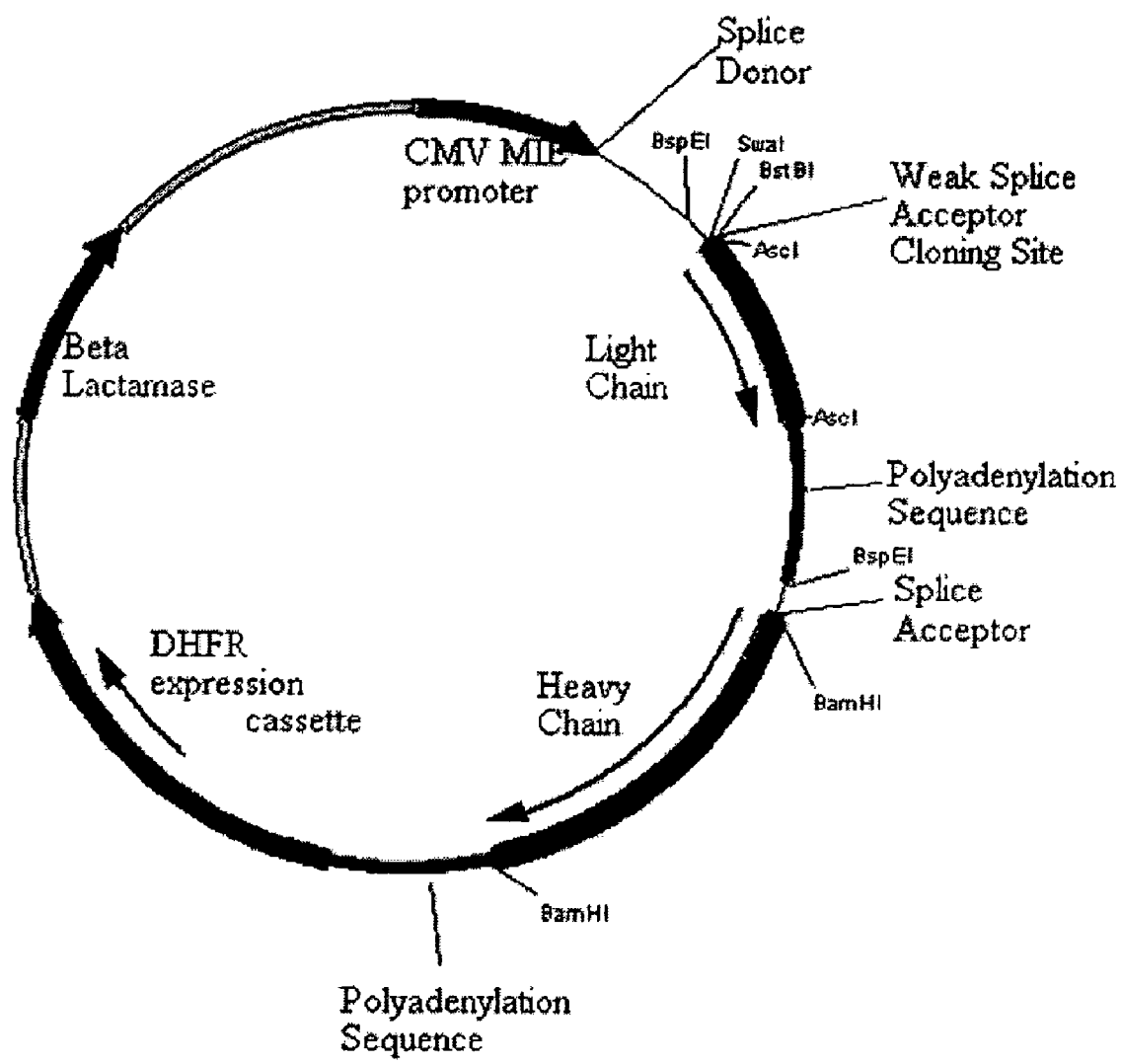

FIG. 3 is a plasmid map of an alternative splicing vector of the invention designed to express an antibody light and heavy chain from a single promoter for the production of an antibody in eukaryotic cells. The plasmid map also indicates the position and orientation of splice sites, cloning sites, polyadenylation sequences, and markers for selection in eukaryotic cells (DHFR) and propagation in prokaryotic cells (beta-lactamase). See also SEQ ID NO: 29, which provides the sequence of the vector backbone.

FIG. 4 shows the sequence of the splice sites of the first splice acceptors tested, intron and exon regions (respectively, lower case and upper case), and corresponding plasmid designations and sequence identifiers.

DETAILED DESCRIPTION OF THE INVENTION

In order to provide a clear understanding of the specification and claims, the following definitions are conveniently provided below.

Definitions

The terms "first polypeptide" or "second polypeptide" refer to polypeptides whose coexpression is desired. These include, for example, polypeptide "chains" of multimeric proteins comprised of multiple polypeptide subunits. These multimeric proteins can be those found in nature, for example, those described in the art. Of course, the the terms "first polypeptide" and "second polypeptide" may also be used in the future to describe multimeric proteins that have not yet been described in the art. These multimeric proteins can also be artificial, e.g. comprised of polypeptides not normally found associated in nature. Further, the polypeptides may not associate together, but be co expressed for some functional purpose, for example, the coexpression of a selectable marker and a polypeptide of interest. Further, the polypeptides can be native sequences or mutated, such as by the addition, deletion, or substitution of amino acids. A person of ordinary skill in the art would readily recognize the suitability of the vectors of the present invention for a broad spectrum of polypeptides and would be able to adapt the vectors for use with these polypeptides using standard molecular biology techniques.

The term "antibody" or "antibody fragment" refers to assemblies of polypeptides or polypeptide fragments, which have binding activity for a target polypeptide or receptor or have a desired effectors function. Typically, such assemblies include at least the variable region of an antibody light chain and heavy chain, for example a Fib fragment, or two antibody light chains and two antibody heavy chains, the four chains together forming a tetrameric antibody (L:H:H:L) the variable regions of which can bind an antigen. The antibodies of the invention can be of any form known in the art, for example, murine, chimeric, humanized, human, or synthetic. The antibodies of the invention may also be modified to have other features such as altered glycosylation sites or Fc regions.

The term "UTR" means untranslated region and refers to a segment of nucleic acid sequence which is transcribed into an untranslated region of the pre-mRNA and mature mRNA. A 5' UTR typically serves as the 5' end of the transcript which is modified or "capped" with a 7-guano, 7-methylguanosine cap which initiates translation of the mRNA transcript into a polypeptide.

The term "expressed in a ratio" refers to the production ratio of a gene product expressed either as a transcript or polypeptide. The determination of the ratio is typically determined using art recognized techniques such as reverse transcriptase polymerase chain reaction (RT-PCR) or Northern blots (for measuring the relative amounts of transcripts) or immunoblot or enzyme linked immunosorbent assay (ELISA) techniques (for measuring relative amounts of polypeptides).

In certain embodiments, the first and second polypeptides are expressed in a ratio of about 20:1 to about 1:20, about 15:1 to about 1:15, about 12:1 to about 1:12, about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2, or about 1:1. In particular embodiments, the first and second polypeptides are expressed in a ratio of about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19 and/or about 1:20.

The term "first exon" refers to a coding sequence or sequence of nucleic acid that encodes a polypeptide or polypeptide region and the term "second exon" refers to a different second coding sequence or sequence of nucleic acid that encodes a second polypeptide region. First and second exons of the present invention also comprise a 5' splice acceptor sequence.

The term "host cell" or "eukaryotic host cell" refers to any eukaryotic cell which produces or expresses the gene products of the first and second exons, using the expression system of the invention. This includes, for example, mammalian cells such as baby hamster kidney cells, fibroblasts, myeloma cells (e.g., NS0 cells), human PER.C6 cells, or Chinese hamster ovary (CHO) cells. Insect cells useful for expression include, for example, *Spodoptera frugiperda* (Sf9) cells, *Tricoplusia ni* (Tn. TnHigh-Five) cells, or *Bombyx mori* (BMN) cells. Yeast cells useful for expression include, for example, *Saccharomyces* cells, *Schizosaccharomyces* cells and *Pichia* cells. Such cells are readily accessible from public and commercial sources, such as the American Type Culture Collection (ATCC, Manassas, Va.).

The term "intron" refers to a segment of nucleic acid sequence that is transcribed and is present in the pre-mRNA but excised by the splicing machinery based on the sequences of the splice donor and splice acceptor(s) and therefore not present in the mature mRNA transcript.

The term "operably linked" refers to a juxtaposition wherein the components are in a relationship permitting them to function in their intended manner (e.g., functionally linked).

The term "polyadenylation signal" refers to a nucleic acid sequence present in the RNA transcript that allows for the transcript, when in the presence of the enzyme polyadenyl transferase, to be polyadenylated. Many polyadenylation signals are known in the art and are useful for the present invention. Examples include the human variant growth hormone polyadenylation signal, the SV40 late polyadenylation signal and the bovine growth hormone polyadenylation signal.

The term "promoter" refers to a minimal sequence sufficient to direct transcription, preferably in a eukaryotic cell. Promoters for use in the invention include, for example, viral, mammalian, insect and yeast promoters that provide for high levels of expression, e.g., the mammalian cytomegalovirus or CMV promoter, the SV40 promoter, or any promoter known in the art suitable for expression in eukaryotic cells.

The term "splice site" refers to specific nucleic acid sequences that are capable of being recognized by the spicing machinery of a eukaryotic cell as suitable for being cut and/or ligated to a corresponding splice site. Splice sites allow for the excision of introns present in a pre-mRNA transcript. Typically the 5' portion of the splice site is the referred to as the splice donor and the 3' corresponding splice site is referred to as the acceptor splice site. The term splice site includes, for example, naturally occurring splice sites, engineered splice sites, for example, synthetic splice sites, canonical or consensus splice sites, and/or non-canonical splice sites, for example, cryptic splice sites.

The term "splice with" refers to the splice donor interacting with a splice acceptor to allow splicing of the transcript by the splicing machinery (e.g., the spliceosome). As described supra, splicing is the excision of a portion of the transcript (the intron) bounded by the splice donor and splice acceptor. For each transcript, the splice donor splices with only one splice acceptor. For alternative splicing, within the pool of transcripts the splice donor splices with more than one splice acceptor. For instance, the splice donor may splice with a first splice acceptor for one transcript, but on another transcript, the splice donor may splice with a second splice acceptor, generating a heterogeneous pool of transcripts.

The term "spliced transcript" refers to an RNA transcribed from the alternative splicing vector of the invention comprising a first or second exon and which has undergone splicing between the splice donor and either of the first or second splice acceptors.

The term "vector" refers to a nucleic acid molecule (either DNA or RNA) capable of conferring the expression of a gene product when introduced into a host cell or host cell extract. This term is interchangeable with "alternative splicing vector", "expression vector", "expression cassette" or "construct". Such vectors or expression cassettes or constructs may comprise the alternative splicing elements of the present invention as well as additional sequences for the propagation of the vector in cells, the entry of the vector into cells and subsequent expression, selectable markers, or any other functional elements. Such elements are well known in the art and can be interchanged as needed using standard molecular biology techniques.

The term "viral vector" or variations thereon (such as "adenoviral vector") refers to an attenuated or replication-deficient viral particle comprising the alternative splicing vector or expression cassette or construct of the invention. As described in more detail below, such viral vectors are useful for inserting the alternative splicing vector or expression cassette or construct of the invention into host cells.

DETAILED DESCRIPTION

1. Overview

The invention provides, in part, a method for expressing two or more gene products in a eukaryotic cell by providing a vector or expression cassette or construct comprising a single promoter driving the expression of two or more exons that have been engineered to be alternatively spliced into two or more expressible transcripts. Thus, the vector or expression cassette or construct is suitable for expressing two or more polypeptides, and in particular, polypeptide multimers, for example antibodies (or antibody fragments) that are typically an assembly of two light chain and two heavy chain antibody polypeptides.

Moreover, because the vector or expression cassette or construct of the invention uses a single promoter to drive expression of a pre-mRNA, which is then alternatively spliced into two or more gene products, the invention avoids the use of multiple vectors, promoter competition from the use of multiple promoters, or differential activity from independent promoters.

Additionally, through the use of multiple splice acceptors, the invention has the advantage of providing for the expression of multiple gene products in a eukaryotic cell at a desired ratio such that, for example, the resultant assembly of polypeptides, for example a tetrameric antibody, is efficiently produced.

Further, the present invention provides for altering the ratio of the expression of the encoded polypeptides by changing the sequence of the splicing elements, particularly the first splice acceptor. The ability to alter the ratio of the expressed polypeptides allows for more efficient multimerization or other functional aspect of the polypeptides by providing the polypeptides in optimal amounts. Thus, the vector or expression cassette or construct of the present invention allows for the expression of the polypeptides in sufficient amounts to produce one or more desired proteins.

Thus, the invention also provides for vectors suitable for the expression of polypeptide multimers, e.g., antibodies, using alternative splicing as well as cells comprising the vector and antibodies produced from such cells, and their use in, for example, prognosing, diagnosing, preventing, ameliorating or treating a disorder or disease in a subject, for example, a human patient.

Father, the invention provides for vectors suitable for the expression of the polypeptides in vivo, by either delivery of the vector to the subject directly or through ex vivo techniques.

Figure 1:
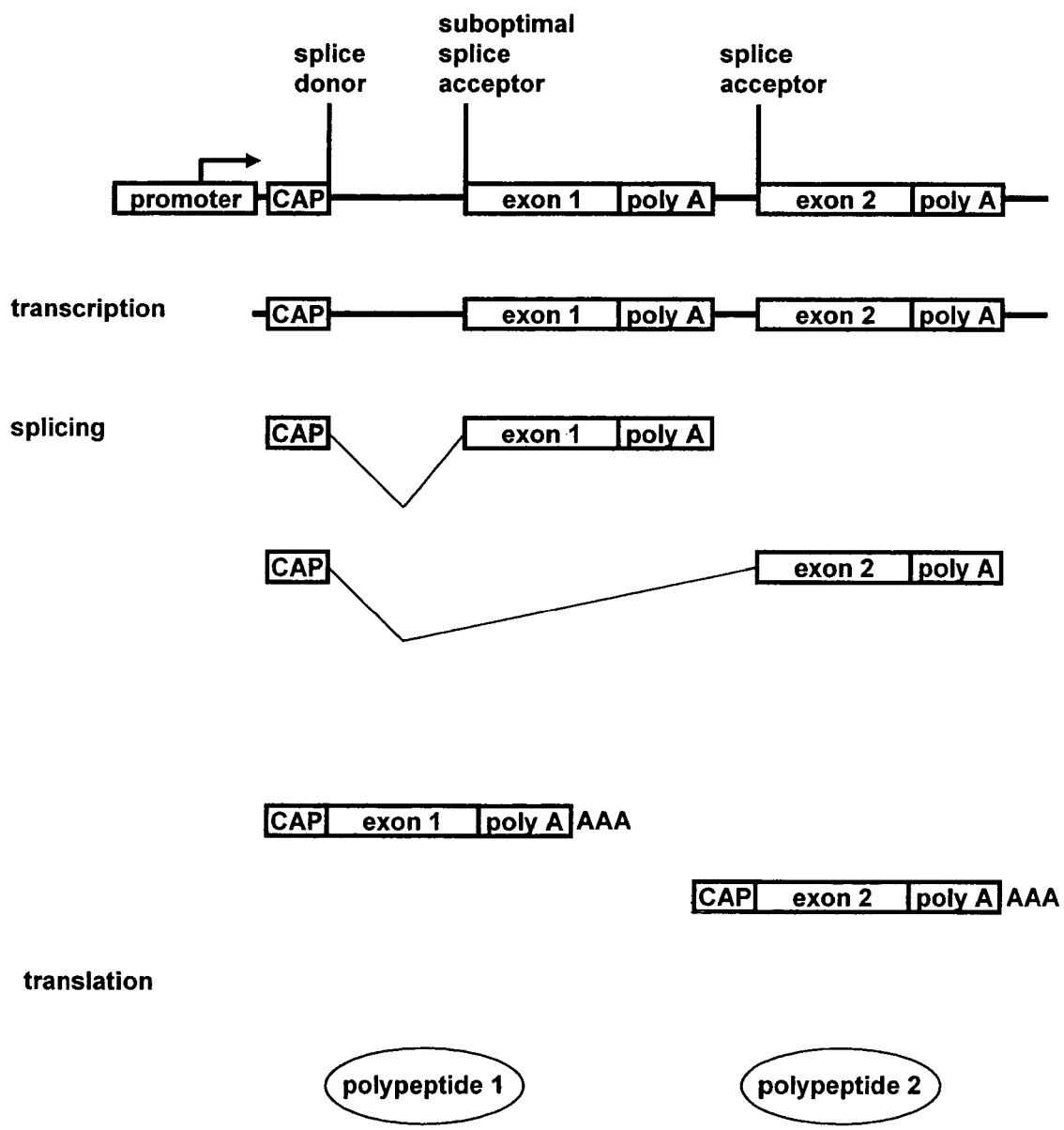
FIG. 1 shows a schematic of the structural and functional aspects of an alternative splicing vector of the invention which is designed to allow for a single promoter to drive the transcription of a single pre-mRNA which can then be alternatively spliced into two or more transcripts. The two or more transcripts are then translated into two or more corresponding polypeptides.

2. Vector or Expression Cassette or Construct Design for Expressing Polypeptide Multimers The methods of the invention employ the use of a vector comprising (in a 5' to 3' or downstream direction) a promoter; a 5' untranslated (UTR) region (which may or may not include coding sequence); a single 5' splice donor; an intron ending with a 3' splice acceptor that is used with preferably about a 5 to 95% efficiency (depending on the desired ratio of products) (exemplary 3' splice acceptor efficiencies include, but are not limited to, 5%, 10%, 15%, 20%, 25%, 30%, 35%, 40%, 45%, 50%, 55%, 60%, 65%, 70%, 75%, 80%, 85%, 90% and 95%); an exon containing the first gene and, optionally, a polyadenylation signal; an intron sequence ending with a 3' splice acceptor which is greater than 50% efficient (in preferred embodiments, the 3' splice acceptor is greater than 75% efficient (e.g., 80%, 85%, 90%, 95% or 100%), greater than 85% efficient (e.g., 90%, 95% or 100%), greater than 90% efficient (e.g., 91%, 92%, 93%, 94%, 95%, 96%, 97%, 98%, 99% or 100%), or, in a highly preferred embodiment, greater than 95% efficient (e.g., 96%, 97%, 98%, 99% or 100%)); and an exon containing the second gene, and optionally, a polyadenylation signal (see FIG. 1). The vector, expression cassette or construct of the present invention can be introduced into a host cell where it produces alternatively spliced mRNA transcripts. These two or more mRNA transcripts encode distinct polypeptides, which are then expressed in sufficient amounts to produce one or more desired multimeric proteins. The ratio of the two or more products can be, if desired, altered through the selection of suitable splice sites, e.g., a weaker or stronger splice acceptor. In particular embodiments, the ratio of the two or more products can be altered through selection of only the first splice acceptor.

Typically, pre-mRNA splicing involves the precise removal of intron sequences and is in part based on the recognition of specific sequences, i.e., donor and acceptor splice sites, at the intron-exon boundaries by the splicing machinery, e.g. the spliceosome. These boundary sequences typically fit the consensus sequences of MAG/GuRAGU (SEQ ID NO: 30) for the 5' end of the intron and $Y_{10}$NCAG/G (SEQ ID NO: 31) for the 3' end of the intron (where M=A or C, underlined are invariant nucleotides, $Y_{10}$=10 consecutive C or T nucleotides, and N=any nucleotide). Sequences within the introns and exons as well as intron size have also been shown to play a role in the efficiency of splicing (see, e.g., Chabot, B. Trends in Genetics, 12:472-478 (1996)).

In certain embodiments of the present invention, alternative splicing can regulate the expression of each polypeptide encoded by the exons of the vector or expression cassette or construct of the invention. For each individual spliced transcript, the splice donor splices with only one splice acceptor or not at all. However, alternative splicing forms a heterogeneous pool of transcripts as the splice donor may splice with the first splice acceptor on one transcript, and splice with a second splice acceptor on another transcript. Thus, the splicing of a single splice donor to multiple splice acceptors will regulate the levels of the spliced transcripts of the first and second (or more) exons generated from a vector or expression cassette or construct of the present invention in a cell. The relative amounts of the differently spliced transcript levels will depend on how often the splice donor is joined with a particular splice acceptor, which is referred to as the efficiency of the splicing event. The more often a particular splicing event occurs in a pool of transcripts, then the splice donor and splice acceptor associated with that splicing event are said to be more efficient or strong.

In certain embodiments of the present invention, it is preferable that the splice donor and 3' terminal splice acceptor (e.g., the second splice acceptor) are highly efficient so that overall splicing is highly efficient and the strength of the first splice acceptor controls the relative levels of spliced exon transcripts. Translation of the unspliced transcript is typically very inefficient, so maximal splicing promotes polypeptide expression. For example, if the splice donor and second splice acceptor are highly efficient, most of the nascent mRNA will be spliced. If the first splice acceptor is strong (i.e., efficient), then relatively high levels of spliced transcripts comprising the first exon will be present within the cell, leading to a high ratio of expression of the first polypeptide compared to the second polypeptide. If the first splice acceptor is weaker, then relatively low levels of spliced transcripts comprising the first exon will be present within the cell, leading to a low ratio of expression of the first polypeptide compared to the second polypeptide. Because translation is highly dependent on the levels of spliced transcript comprising a given exon, expression of the polypeptide encoded by the first or second exon is dependent on the levels of splicing utilizing the splice acceptor immediately upstream of that exon. Therefore, in certain embodiments, because splicing affects the levels of the mature transcripts comprising each exon encoded by a vector or expression cassette or construct of the invention, alternative splicing is used to regulate the expression of the polypeptides encoded by the exons.

Splice donors and splice acceptors are well known in the art and any may be utilized in the present invention. These elements can be found, inter alia, in the art or derived from consensus sequences, either empirically by inserting, deleting or substituting nucleotides, or by using software capable of predicting splicing sequences, such as Netgene2 version 2.4. Such splicing elements can be tested for suitability in the present invention, such as by using the methods described in the examples. In part, the present invention incorporates and improves upon such sequences to achieve, through genetic engineering, alternative splicing of two or more desirable recombinant gene products in eukaryotic cells.

The vector or expression cassette or construct of the invention is useful for expressing a variety of heteromultimeric proteins. Examples include, but are not limited to, heterodimers such as the glycoprotein hormones (e.g. chorionic gonadotropin (CG), thyrotropin (TSH), lutropin (LH), and follitropin (FSH)) or members of the integrin family. Heterotetramers consisting of two pairs of identical subunits could also be used. Examples of appropriate heterotetramers include antibodies, the insulin receptor (alpha2 beta2) and the transcription initiation factor TFIIE (alpha2 beta2). Further, using a splice acceptor pair that generates a 2:1 ratio of expression, the vector or expression cassette or construct can be used for the expression of heterotrimers such as lymphotoxin alpha1 beta2. Altering the expression ratio by combining different splice acceptors can generate vectors or expression cassettes or constructs capable of expressing multimers in different ratios, allowing for the efficient expression of many different heteromultimeric proteins. In certain embodiments, expression ratios are predicted based on the sequence of the splice donor and/or acceptor signals. In other embodiments, expression ratios are determined empirically.

Moreover, the genetic sequences useful for producing polypeptide multimers, for example, antibodies, using the alternative splicing system of the invention may be obtained from a number of different sources. For example, a variety of human protein genes are available in the form of publicly accessible genetic sequence deposits and/or deposits of plasmids, clones, cells, and the like. Many sequences of proteins and protein-encoding genes have been published and suitable genes can be synthesized from these sequences such as described herein. Alternatively, protein-producing cell lines may be selected and cultured using art recognized techniques. In other embodiments, genetic sequences are obtained through access to subscription databases. One of ordinary skill in the art would know of many methods appropriate to obtain genetic sequence information.

For example, antibody-encoding RNA may be isolated from the original antibody-producing hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Techniques suitable for these purposes are familiar to one of ordinary skill in the art.

The cDNAs that encode the light and the heavy chains of the antibody may be made, either simultaneously or separately, using reverse transcriptase and DNA polymerase in accordance with well-known methods. It may be initiated by consensus constant region primers or by more specific primers based on, for example, the published antibody light and heavy chain DNA and amino acid sequences. As discussed above, PCR also may be used to isolate DNA clones encoding the antibody light and heavy chains. In this case libraries may be screened by consensus primers or larger homologous probes, such as mouse constant region probes.

Alternatively, antibodies and antibody fragments may be synthesized using sequences derived from well-known computer modeling techniques. Such modeling techniques can be used to predict antibody sequences that, in the context of a given antibody framework defined by conserved amino acid sequences, would bind a predicted ligand structure. By using this known relationship, a person of skill in the art can design the amino acid sequence of a desired antibody or antibody fragment, then synthesize the nucleic acid molecules encoding the desired polypeptides. Such designed antibody or antibody fragments are referred to as "synthetic".

The inventive compositions and methods of the present invention are suitable for any antibody, or indeed any multichain or multimeric protein. Oligonucleotide synthesis techniques compatible with this embodiment of the invention are well-known by one of ordinary skill in the art, and can be carried out using any of several commercially available automated synthesizers. In addition, DNA sequences encoding several types of heavy and light chains set forth herein can be obtained through the services of commercial DNA vendors. The genetic material obtained using any of the foregoing methods may then be altered or modified to provide antibodies compatible with the present invention and the desired use of such antibodies.

A variety of different types of antibodies may be expressed according to the invention. For example, antibody or antibody fragments with specific immunoreactive activity to an antigen, e.g. a tumor associated antigen, pathogen, or self-antigen involved in autoimmune disease. The antibody (or fragment thereof) may be modified such that one or more constant regions are deleted or otherwise altered so as to provide desired functional activity such as serum half-life, or effectors function. Many such antibodies are described in Kuby, *J. Immunology*, 3$^{rd}$ ed., W. H. Freeman and Co. (1997).

Figure 2:
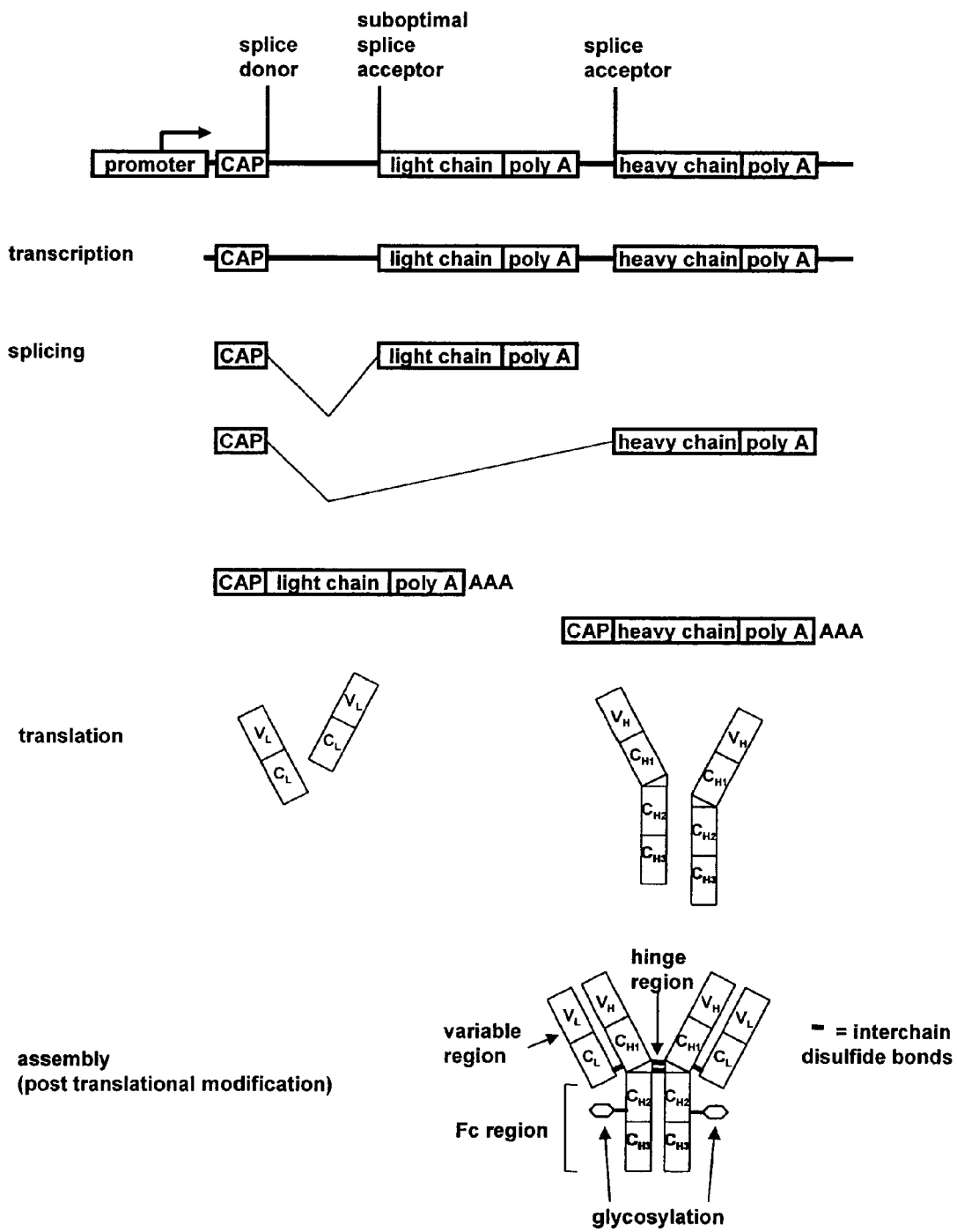
FIG. 2 shows a schematic of an expression vector of the invention when used to express an antibody light and heavy chain which are then assembled to form a mature tetrameric antibody.

Antibodies suitable for expressing in a eukaryotic cell using the method of the invention include the five distinct classes of antibody: IgA, IgD, IgG, IgE, and IgM. While all five classes are within the scope of the present invention, the following discussion is generally directed to the class of IgG molecules. One of ordinary skill in the art could easily adapt the following discussion to the other classes of immunoglobulins. IgG molecules typically comprise two identical antibody light chains of a molecular weight of approximately 23 kD each, and two identical antibody heavy chains of a molecular weight of 53-70 kD each. Interchain disulfide bonds, in a configuration as shown in FIG. 2, join the four chains. In addition, both the antibody light and heavy chains are divided into regions of structural and functional homology. The terms "constant" and "variable" are used functionally. In this regard, it will be appreciated by one of ordinary skill in the art that the variable domains of both the antibody light (VL) and heavy (VH) chains determine antigen recognition and specificity. Conversely, the constant domains of the light chain (CL) and the heavy chain (CH1, CH2 or CH3) confer important biological properties such as secretion, transplacental mobility, Fc receptor binding, complement binding, and other effectors functions.

Light chains are classified as either kappa or lambda chains. Each heavy chain class may be bound with either a kappa or lambda light chain. In general, the light and heavy chains are covalently bonded to each other, and the "tail" portions of the two heavy chains are bonded to each other by covalent disulfide linkages when the immunoglobulins are generated either by hybridomas, B cells, or genetically engineered host cells (see FIG. 2). At the N-terminus is a variable region and at the C-terminus is a constant region. Heavy chains are classified as gamma, mu, alpha, delta, or epsilon, with some subclasses among them. It is the nature of this chain that determines the "class" of the antibody as IgA, IgD, IgE IgG, or IgM. The immunoglobulin subclasses (isotypes) e.g., IgG1, IgG2, IgG3, IgG4, IgA1 are well characterized and are known to confer functional specialization. It is understood that the first exon or the second exon of the present invention can be used to alternatively encode either a light or heavy antibody chain so long as the resultant vector encodes one light chain and one heavy chain.

The antigen-binding site is defined by three complementarity determining regions (CDRs) on each of the VH and VL chains. The six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a beta-sheet conformation and the CDRs form loops connecting, and in some cases forming part of, the beta-sheet structure. Thus, the framework regions act to form a scaffold that provides for positioning of the six CDRs in correct orientation by inter-chain, non-covalent interactions. The antigen-binding site formed by the positioned CDRs defines a surface complementary to the epitope on the immunoreactive antigen. This complementary surface promotes the non-covalent binding of the antibody to the immunoreactive antigen epitope.

Antibody fragments are suitable for expression using the alternative splicing vectors or expression cassettes or constructs of the invention. Such fragments are any portion or portions of an antibody desired, and may include, e.g., Fab fragments F(ab')$_2$ fragments, and Fc fragments. Further, antibody fragments may include single chain antibodies or other antibody-derived polypeptides comprising less than the full length, tetrameric antibody protein.

It will be appreciated by one of ordinary skill in the art that antibodies expressed using the alternative splicing vectors or expression cassettes or constructs of the invention may comprise any type of variable region that provides for the association of the antibody with the selected antigen. In this regard, the variable region may comprise or be derived from any type of mammal that can be induced to mount a humoral response and generate immunoglobulins against the desired antigen. As such, the variable region of the modified antibodies may be, for example, of murine, non-human primate, or human. When derived from a different species, typically a murine variable region fused to human constant regions, the antibody is referred to as a chimeric antibody. In preferred embodiments, both the variable and constant regions of the antibodies are human. In other selected embodiments the variable regions of compatible antibodies (usually derived from a non-human source) may be engineered or specifically tailored to improve the binding properties (e.g., affinity maturation) or reduce the immunogenicity of the molecule. In this respect, variable regions useful in the present invention can be humanized or otherwise altered through the inclusion of imported DNA or amino acid sequences. Such human antibodies, having CDRs grafted from another species, are referred to as humanized antibodies. Further, variable regions may be engineered, or synthetic, as previously described. Any of the foregoing antibodies may be further modified to have altered glycosylation sites, sites suitable for pegylation, and/or sites that confer an altered effectors function to the antibody, e.g., altered complement binding, altered Fc receptor binding, and/or altered immune cell interaction activity.

For the purposes of this invention, numerous alternative splicing expression vector systems can be employed. For example, the alternative splicing vector or expression cassette or construct of the invention can contain DNA elements which are derived from animal viruses such as a human or bovine papillomavirus virus, a polyoma virus, an adenovirus, a vaccinia virus, a baculovirus, a retrovirus (e.g., HIV), a cytomegalovirus, or an SV40 virus. Additionally, cells that can integrate the alternative splicing vector or expression cassette or construct into their chromosomes or maintain the vector or expression cassette or construct episomally can be selected by introducing one or more markers that allow selection of the transfected host cells. The selectable marker gene can either be directly linked to the DNA sequences to be expressed, or introduced into the same cell by cotransfection. Suitable host cells for introducing the vectors or expression cassettes or constructs of the invention are discussed below.

3. Expression of Polypeptide Multimers in Eukaryotic Cells in Culture

The alternative splicing vector or expression cassette or construct of the invention can be introduced into an appropriate host cell using technologies that are well-known to one of ordinary skill in the art. These include, for example, transfection (including electrophoresis and electroporation), protoplast fusion, calcium phosphate precipitation, cell fusion with enveloped DNA, microinjection, and infection with virus (see, e.g., Ridgway, A. A. G. "Mammalian Expression Vectors" Chapter 24.2, pp. 470-472 Vectors, Rodriguez and Denhardt, Eds. (Butterworths, Boston, Mass. 1988). As mentioned above, the vectors or expression cassettes or constructs of the invention can be integrated into the chromosome of the host cell, maintained episomally, or expressed transiently. The transformed cells are grown under conditions appropriate to the production of the polypeptides encoded theeerein, e.g., the antibody, light and heavy chains, and assayed for polypeptide synthesis. Exemplary assay techniques for identifying and quantifying polypeptide synthesis include, e.g., enzyme-linked immunosorbent assay (ELISA), fluorescence resonance energy transfer (FRET), radioimmunoassay (RIA), fluorescence-activated cell sorter analysis (FACS), and immunohistochemistry.

The host cell line used for protein expression is preferably of eukaryotic origin, for example mammalian origin or, alternatively, a yeast or insect. Exemplary host cell lines include, for example, Chinese Hamster Ovary (CHO) lines, HeLa (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), NS0 (myeloma), (bovine endothelial cells), RAJI (human lymphocyte), 293 (human kidney), PER.C6 (human), *Spodoptera frugiperda* (Sf9) (insect), *Tricoplusia ni* (Tn. TnHigh-Five) (insect), *Bombyx mori* (BMN) (insect), *Saccharomyces* (yeast), *Schizosaccharomyces* (yeast), and *Pichia* (yeast). Host cell lines are typically available from commercial services, such as the American Tissue Culture Collection or from published literature.

In vitro production allows scale-up to give large amounts of the desired polypeptide produced using the alternative splicing system of the present invention, preferably an antibody. Techniques for eukaryotic, e.g., mammalian and yeast cell cultivation under tissue culture conditions are well-known by those of ordinary skill in the art and include homogeneous suspension culture, e.g. in an airlift reactor or in a continuous stirrer reactor, or immobilized or entrapped cell culture, e.g. in hollow fibers, microcapsules, on agarose microbeads, ceramic cartridges or in fermentors. For isolation and recovery of the multimeric proteins produced according to the invention, in particular with respect to antibodies, the proteins (e.g., immunoglobulins) in the culture supernatants can first be concentrated, e.g., by precipitation with ammonium sulfate, dialysis against hygroscopic material such as PEG and filtration through selective membranes. If necessary and/or desired, the concentrated solutions of the multimeric proteins (e.g., multivalent antibodies) are purified by the customary chromatography methods, for example gel filtration, ion-exchange chromatography, chromatography over DEAE-cellulose, or immunoaffinity chromatography (e.g., Protein A or Protein G).

The invention further contemplates the expression of any antibody light and heavy chain sequence which when expressed using the alternative splicing system of the invention, associate to produce a functional antibody, e.g., one that specifically binds to a target antigen, such as a tumor associated antigen, pathogen, or self-antigen or has a desired effectors function.

Importantly, the copy number of the antibody light and heavy chain genes in the alternatively spliced construct may be selected such that the preferred ratio of light/heavy chain are obtained. In certain embodiments, the light chain is expressed at levels which typically range from about 10/1, about 5/1, about 3/1 or about 1/1 relative to the heavy chain. In related embodiments, the light and heavy polypeptides are expressed in a ratio of about 20:1 to about 1:20, about 15:1 to about 1:15, about 12:1 to about 1:12, about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2, or about 1:1. In particular embodiments, the light and heavy polypeptides are expressed in a ratio of about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19 and/or about 1:20.

The invention also provides a method for selecting any desired ratio by screening vectors having different splice sites such that, e.g., in a given cell line, the desired ratio is achieved (see, e.g., Example 2). This is especially critical when efficiently expressing an antibody because it has been observed that certain expression levels of light chain can be instrumental in directing the appropriate assembly of the antibody heavy and light chains, and excessive unpaired heavy chain can induce cell toxicity. Moreover, the light chain is also critical in directing folding of the assembled antibody heavy and light chains to produce a functional antigen-binding antibody in the endoplasmic reticulum. Accordingly, in certain embodiments, the antibody light chain is typically expressed from about 10/1 to 1/1 relative to the antibody heavy chain (exemplary light/heavy chain ratios include, but are not limited to, about 10/1, 9/1, 8/1, 7/1, 6/1, 5/1, 4/1, 3/1, 2/1 and 1/1).

In certain embodiments, an antibody that is expressed according to the subject expression system may be specific to any desired antigen. Preferably, the antibody will be a functional antibody that elicits a therapeutic effect, such as an antibody useful for treating an autoimmune, inflammatory, infectious, allergic, or neoplastic disease. The antibody may be combined with other therapeutic agents for synergistic effects. For example, the antibody may be combined with, e.g., other antibodies, small molecules, or a radioactive source for use as a cancer chemotherapeutic agent.

In certain embodiments, the alternative splicing vectors or expression cassettes or constructs of the present invention are used in combination with other vectors or expression cassettes or constructs that do not intentionally rely on alternative splicing to express multiple polypeptides.

4. Pharmaceutical Compositions

The invention also provides, inter alia, therapeutic compositions comprising multimeric proteins expressed using methods and/or vectors or expression cassettes or constructs of the present invention for the treatment of a subject or patient in need thereof. The compositions of the present invention can be used to treat a subject (i.e. a patient) in need thereof via administration of therapeutic polypeptides produced by the methods of the invention or by gene therapy comprising the alternative splicing vector or expression cassette or construct of the invention. A subject in need thereof is a subject suffering, or at risk of suffering, from a disease, disorder or condition that can be treated or prevented by administering a composition of this invention. That subject may be a mammalian subject. A preferred subject is a human subject.

In certain embodiments, such therapeutic compositions include such multimeric proteins in a pharmaceutically acceptable carrier. In preferred embodiments, such therapeutic compositions include at least one recombinant antibody or antibody fragment produced according to the invention in a pharmaceutically acceptable carrier. A "pharmaceutically acceptable carrier" refers to at least one component of a pharmaceutical preparation that is normally used for administration of active ingredients. As such, a carrier may contain any pharmaceutical excipient used in the art and any form of vehicle for administration. The compositions may be, for example, injectable solutions, aqueous suspensions or solutions, non-aqueous suspensions or solutions, solid and liquid oral formulations, salves, gels, ointments, intradermal patches, creams, lotions, tablets, capsules, sustained release formulations, and the like. Additional excipients may include, for example, colorants, taste-masking agents, solubility aids, suspension agents, compressing agents, enteric coatings, sustained release aids, and the like.

Agents of the invention are often administered as pharmaceutical compositions comprising an active therapeutic agent and a variety of other pharmaceutically acceptable components. See *Remington's Pharmaceutical Science* (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents include, but are not limited to, distilled water, physiological phosphate-buffered saline, Ringer's solutions, dextrose solution, and Hank's solution. In addition, the pharmaceutical composition or formulation may also include other carriers, adjuvants, or non-toxic, nontherapeutic, nonimmunogenic stabilizers. Typically, such compositions are administered in therapeutically effective amounts, which is an amount sufficient to produce a detectable, preferably medically beneficial, effect on a subject or patient suffering or at risk of suffering from a disease, disorder or condition amenable to treatment with the compositions of the invention.

Multimeric proteins produced according to the present invention can be administered in the form of an injection or implant preparation, which can be formulated in such a manner as to permit a sustained release of the active ingredient. In a preferred embodiment, such multimeric protein is an antibody. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249: 1527 (1990) and Hanes, *Advanced Drug Delivery Reviews* 28:97 (1997)).

5. Prophylactic and Therapeutic Methods

In certain embodiments, the present invention is directed to the production of proteins suitable for the prevention, amelioration or treatment of any disease, disorder or condition. Such disorders or diseases include cancer, precancerous conditions, and genetic disease or condition such as muscular dystrophy. A disease, a disorder or a condition amenable to treatment with the proteins produced by the methods of the present invention includes conditions such as genetic diseases (i.e., a disease condition that is attributable to one or more gene defects), acquired pathologies (i.e., a pathological condition that is not attributable to an inborn defect) and prophylactic processes (i.e., prevention of a disease or of an undesired medical condition). An acquired pathology may be a disease or syndrome manifested by an abnormal physiological, biochemical, cellular, structural or molecular biological state.

A disease, a disorder or a condition amenable to treatment with the proteins produced by the methods of the present invention may be an infection, including viral and bacterial infection, a hyperproliferative disease or disorder, including cancer and pre-cancerous conditions, immunel disorders, such as rheumatoid arthritis, genetic immunodeficiency conditions, such as hyper-IgM syndrome, primary or combined immunodeficiency conditions, including conditions characterized by neutropenia, as well as neurological disorders, cardiovascular disorders, such as ischemia, and endocrine disorders, such as diabetes, thyroid disorders and infertility.

A disease, a disorder or a condition amenable to treatment with the proteins produced by the methods of the present invention may be hyperproliferative diseases or disorders, including cancers. Such diseases or disorders can involve any cells, tissue or organ, including brain, lung, squamous cell, bladder, stomach, pancreas, breast, head, neck, liver, kidney, ovary, prostate, colon, rectum, esophagus, nasopharynx, thyroid and skin. The cancer may be melanoma, lymphoma, leukemia, multiple myeloma, sarcoma or carcinoma. The cancer may be solid tumors or may involve a bodily fluid, such as blood.

A disease, a disorder or a condition amenable to treatment with the proteins produced by the methods of the present invention may be genetically inherited diseases, such as Huntington's disease, bipolar disorder, Parkinson's disease, Carpal Tunnel Syndrome, cystic fibrosis, Pelizaeus-Merzbacher Disease, multiple sclerosis or Duchenne Muscular Dystrophy.

A disease, a disorder or a condition amenable to treatment with the proteins produced by the methods of the present invention may be an infectious disease, such as tuberculosis, malaria, yellow fever, or a disease caused by infection by hepatitis B virus, herpesviruses, human immunodeficiency virus, etc.

In particular embodiments, the present invention is also directed, inter alia, to the production of antibodies or antibody fragments suitable for the prevention or treatment of a disorder or disease, e.g., a disorder or disease of the immune system.

Accordingly, in certain embodiments, the antibodies or antibody fragments of the present invention are useful in the prevention or treatment of immune disorders including, for example, glomerulonephritis, scleroderma, cirrhosis, multiple sclerosis, lupus nephritis, atherosclerosis, inflammatory bowel diseases, allergies or rheumatoid arthritis. In another embodiment, the antibodies or antigen-binding fragments of the invention can be used to treat or prevent inflammatory disorders, including, but not limited to, Alzheimer's, severe asthma, atopic dermatitis, cachexia, CHF-ischemia, coronary restinosis, Crohn's disease, diabetic nephropathy, lymphoma, psoriasis, fibrosis/radiation-induced, juvenile arthritis, stroke, inflammation of the brain or central nervous system caused by trauma, and ulcerative colitis.

Other inflammatory disorders which can be prevented or treated with the antibodies or antibody fragments produced according to the invention include inflammation due to corneal transplantation, chronic obstructive pulmonary disease, hepatitis C, multiple myeloma, and osteoarthritis. In another embodiment, the antibodies or antigen-binding fragments of the invention can be used to prevent or treat neoplasia, including, but not limited to bladder cancer, breast cancer, head and neck cancer, Kaposi's sarcoma, melanoma, ovarian cancer, small cell lung cancer, stomach cancer, leukemia/lymphoma, and multiple myeloma. Additional neoplasia conditions include, cervical cancer, colo-rectal cancer, endometrial cancer, kidney cancer, non-squamous cell lung cancer, and prostate cancer.

In another embodiment, the antibodies or antibody fragments of the invention can be used to prevent or treat neurodegenerative disorders, including, but not limited to Alzheimer's, stroke, and traumatic brain or central nervous system injuries. Additional neurodegenerative disorders include ALS/motor neuron disease, diabetic peripheral neuropathy, diabetic retinopathy, Huntington's disease, macular degeneration, and Parkinson's disease.

In clinical applications, a subject is identified as having or at risk of developing one of the above-mentioned conditions by exhibiting at least one sign or symptom of the disease or disorder. At least one antibody or antibody fragment thereof of the invention or compositions comprising at least one antibody or antigen-binding fragment thereof of the invention is administered in a sufficient amount to treat at least one symptom of a disease or disorder, for example, as mentioned above.

Accordingly, a protein of the invention is suitable for administration as a therapeutic reagent to a subject under conditions that generate a beneficial therapeutic response in a subject, for example, for the prevention or treatment of a disease or disorder, as for example, described herein.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w purity and, more preferably at least 90% or about 95% w/w purity. However, using conventional protein purification techniques, for example as described herein, homogeneous peptides of at least 99% w/w can be obtained.

The methods can be used on both asymptomatic subjects and those currently showing symptoms of disease. The antibodies used in such methods can be human, humanized, chimeric or nonhuman antibodies, or fragments thereof (e.g., antigen binding fragments) and can be monoclonal or polyclonal.

In another embodiment, the invention features administering an antibody, produced according to a method of the invention, with a pharmaceutical carrier as a pharmaceutical composition. Alternatively, the antibody can be administered to a subject by administering a polynucleotide encoding at least one antibody chain. The polynucleotide is expressed to produce the antibody chain in the subject. Accordingly, the polynucleotide encodes the heavy and light chains of the antibody. The polynucleotide is expressed to produce the heavy and light chains in the subject. In exemplary embodiments, the subject is monitored for the level of administered antibody in the blood of the subject.

6. Gene Delivery

The present invention also encompasses gene therapy whereby nucleic acid comprising the alternative splicing vector is provided to a patient in need thereof. The same diseases, disorders and conditions can be treated, ameliorated or prevented as described above for treatment with polypeptides produced by the methods of the invention. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12(4): 335-356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. Alternatively, genes conferring immunity can be transferred, such as by providing antibodies against a particular antigen in the alternative splicing vector of the invention.

Gene transfer methods for gene therapy fall into three broad categories-physical (e.g., electroporation, direct gene transfer and particle bombardment), chemical (lipid-based carriers or other non-viral vectors) and biological (virus-derived vector and receptor uptake). For example, non-viral vectors may be used which include liposomes complexed with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the method is the same, but the transfected cells are cells growing in culture, such as tissue culture cells, and not cells from the individual patient.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use mechanical or chemical methods may be used for in vivo insertion of the nucleic acids of the invention.

Mechanical methods of DNA delivery include direct injection of DNA, such as microinjection of DNA into germ or somatic cells, pneumatically delivered DNA-coated particles, such as the gold particles used in a "gene gun," and inorganic chemical approaches such as calcium phosphate transfection.

Another method, ligand-mediated gene therapy, involves complexing the DNA with specific ligands to form ligand-DNA conjugates, to direct the DNA to a specific cell or tissue.

Chemical methods of gene therapy may involve a chemical to bind to the cell and/or ferry the DNA across the cell membrane, such as fusogenic lipid vesicles such as liposomes or other vesicles for membrane fusion, lipid particles of DNA incorporating cationic lipid such as lipofectin, or polylysine-mediated transfer of DNA. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells and can be engineered to comprise the alternative splicing vector of the present invention. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols (see e.g., Eck, S. L. and J. M. Wilson, "Gene Based Therapy", *Goodman & Gilman's The Pharmacological Basis of Therapeutics*, 9$^{th}$ ed., pp. 77-101, McGraw-Hill, New York (1996)). To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site-specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors and adenoviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by the 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long-term expression of heterologous genes in vivo in some cell types.

Adenoviral vectors are derived from replication incompetent adenoviruses, which are typically contain a deletion in the E1 gene. Such vectors are transfected into cells, such as the 293 human embryonic kidney cell line, which allow replication of E1 deleted adenoviruses. After transfection, the adenoviral vector is allowed to replicate in these specialized helper cells and form infectious particles, which are collected and purified. These particles are capable of infecting a broad range of host cells for expression of the transgene, e.g., the alternative splicing vector of the present invention, but are not capable of replicating without the addition of additional viral factors. To reduce the likelihood of replication-competent adenoviruses contaminating the adenoviral preparation, adenoviral vectors with additional deletions or mutations in the viral genome may be used, such as E1/E3 deleted vectors or "gutless" vectors that have had all or most of the viral genes inactivated. Alternatively, an adenoviral vector containing an inverted protein pIX gene, as described in U.S. Application Nos. 60/621,782 and 60/631,246 may be used.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various or multiple gene products.

Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs.

Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells.

This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoportein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

For example, tumor cells removed from a patient can be transfected with a vector of the present invention expressing anti-tumor polypeptides, and re-introduced into the patient. The transfected tumor cells produce protein levels in the patient that inhibit the growth of the tumor. Patients may be human or non-human animals. Cells may also be transfected by physical or chemical methods known in the art such as electroporation, ionoporation, or via a "gene gun." Additionally, the nucleic acid comprising the alternative splicing vector of the invention may be directly injected, without the aid of a carrier, into a patient. In particular, vector DNA may be injected into skin, muscle or blood.

The gene therapy protocol for transfecting the vector of the invention into a patient may either be through integration of the vector DNA into the genome of the cells, into minichromosomes or as a separate replicating or non-replicating DNA construct in the cytoplasm or nucleoplasm of the cell. Protein expression may continue for a long period of time or may be reinjected periodically to maintain a desired level of the protein in the cell, the tissue or organ or a determined blood level.

7. Treatment Regimes and Dosages

In prophylactic applications, pharmaceutical compositions or medicaments are administered to a subject suffering from a disorder treatable with a recombinant protein of the invention, for example, an immune system disorder, in an amount sufficient to eliminate or reduce the risk, lessen the severity, or delay the outset of the disorder, including biochemical, histologic and/or behavioral symptoms of the disorder, its complications and intermediate pathological phenotypes presenting during development of the disorder. In therapeutic applications, compositions or medicaments are administered to a subject suspected of, or already suffering from such a disorder in an amount sufficient to cure, or at least partially arrest, the symptoms of the disorder (biochemical, histologic and/or behavioral), including its complications and intermediate pathological phenotypes in development of the disorder. The polypeptides of the invention are particularly useful for modulating the biological activity of a cell surface antigen that resides in the blood, where the disease being treated or prevented is caused at least in part by abnormally high or low biological activity of the antigen.

In some methods, administration of compositions of the present invention reduces or eliminates the immune disorder, for example, inflammation. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved.

Effective doses of the compositions of the present invention, for the treatment of the above described conditions vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

The polypeptides and proteins expressed by the alternative splicing vector or expression cassette or construct of the invention described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the polypeptides may be incorporated into biodegradable polymers allowing for sustained release of the compound, the polymers being implanted in the vicinity of where drug delivery is desired, for example, at the site of a tumor or implanted so that the polypeptides are slowly released systemically. Osmotic minipumps may also be used to provide controlled delivery of high concentrations of the polypeptides through cannulae to the site of interest, such as directly into a metastatic growth or into the vascular supply to that tumor. The biodegradable polymers and their use are described, for example, in detail in Brem et al., *J. Neurosurg.* 74:441-446 (1991).

The dosage of the polypeptides of the present invention will depend on the disease state or condition being treated and other clinical factors such as weight and condition of the human or animal and the route of administration of the compound. For treating humans or animals, between approximately 0.5 mg/kilogram to 500 mg/kilogram of the polypeptides can be administered. Depending upon the half-life of the polypeptides in the particular animal or human, the polypeptides can be administered between several times per day to once a week. It is to be understood that the present invention has application for both human and veterinary use. The methods of the present invention contemplate single as well as multiple administrations, given either simultaneously or over an extended period of time.

For passive immunization with an antibody, the dosage ranges from about 0.0001 to 100 mg/kg, and more usually 0.01 to 20 mg/kg, of the host body weight. For example dosages can be 1 mg/kg body weight or 10 mg/kg body weight or within the range of 1-10 mg/kg, preferably at least 1 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Antibody is usually administered on multiple occasions. Intervals between single dosages can be weekly, monthly or yearly. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the subject. In general, human antibodies show the longest half-life, followed by humanized antibodies, chimeric antibodies, and nonhuman antibodies.

The dosage and frequency of administration can vary depending on whether the treatment is prophylactic or therapeutic. In prophylactic applications, compositions containing the present antibodies or a cocktail thereof are administered to a subject not already in the disease state to enhance the subject's resistance. Such an amount is defined to be a "prophylactic effective dose." In this use, the precise amounts again depend upon the subject's state of health and general immunity, but generally range from 0.1 to 25 mg per dose, especially 0.5 to 2.5 mg per dose. A relatively low dosage is administered at relatively infrequent intervals over a long period of time. Some subjects continue to receive treatment for the rest of their lives.

In therapeutic applications, a relatively high dosage (e.g., from about 1 to 200 mg of antibody per dose, with dosages of from 5 to 25 mg being more commonly used) at relatively short intervals is sometimes required until progression of the disease is reduced or terminated, and preferably until the subject shows partial or complete amelioration of symptoms of disease. Thereafter, the patient can be administered a prophylactic regime.

Doses for nucleic acids encoding antibodies range from about 10 ng to 1 g, 100 ng to 100 mg, 1 μg to 10 mg, or 30-300 μg DNA per subject. Doses for infectious viral vectors will vary dpending on the type of viral vector used, but will be between $1\times10^5$ to $1\times10^{20}$ virions per dose in vivo. For in vitro dosages, generally about 0.5 to 100 virions per cell will be used.

Therapeutic agents can be administered by parenteral, topical, intravenous, oral, subcutaneous, intraarterial, intracranial, intraperitoneal, intranasal or intramuscular means for prophylactic and/or therapeutic treatment. The most typical route of administration of a protein drug is intravascular, subcutaneous, or intramuscular, although other routes can be effective. In some methods, agents are injected directly into a particular tissue where deposits have accumulated, for example intracranial injection. In some methods, antibodies are administered as a sustained release composition or device, such as a Medipad™ device. The protein drug can also be administered via the respiratory tract, e.g., using a dry powder inhalation device.

Agents of the invention can optionally be administered in combination with other agents that are at least partly effective in treatment of disorders targeted by the present invention.

The following examples are included for purposes of illustration and should not be construed as limiting the invention. The contents of any patents, patent applications, patent publications (national and international), (specifically including sequence listings) and references cited throughout this specification are hereby incorporated by reference in their entireties.

Exemplification

Throughout the examples, the following materials and methods were used unless otherwise stated.

Materials and Methods

In general, the practice of the present invention employs, unless otherwise indicated, conventional techniques in molecular biology, recombinant DNA technology, and oncology, neurology, and immunology, especially, e.g., antibody technology. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Introduction of Alternative Splicing Vectors into Eukaryotic Cells

For polypeptide expression in eukaryotic cells, vectors of the invention were typically introduced into CHO cells by electroporation in 0.8 ml of HEBS (20 mM Hepes pH 7.05, 137 mM NaCl, 5 mM KCl, 0.7 mM Na2HPO4, 6 mM dextrose) using a 0.4 cm cuvette (BioRad, Hercules, Calif.) at 0.28 kV and 950 uF. About $5\times10^6$ cells were used for each electroporation. After electroporation, cells were allowed to incubate in the cuvette for 5-10 min at room temperature and then transferred to a centrifuge tube containing 10 ml of serum free CHO media and pelleted at 1,000 rpm for 5 min. Cell pellets were then resuspended in 10 ml of serum free CHO media, seeded into T75 flasks, and incubated at 36° C. with 5% $CO_2$ in a humidified incubator. Three to five days after transfection, conditioned media was harvested and antibody titer determined by ELISA. Transfections were performed in duplicate.

Polypeptide Multimer Expression Analysis

Expression analysis was typically carried out using DHFR selection. Stably transfected cells were grown in serum free CHO media lacking nucleosides for approximately two weeks after transfection. Cells transfected with no DNA (negative control) were dead whereas cells containing the selectable marker grew. The specific polypeptide multimer productivity of the cells was assessed by exchanging the media, seeding the cells at $2\times10^5$ to $3\times10^5$ viable cells/ml, and allowing the cells to grow for two to three days after which the antibody titer and the cell densities were determined.

All titers were determined using a FRET assay or an ELISA specific for the variable region of the antibody and/or an ELISA specific for the Fc region of the antibody. Briefly, plates were coated with 50 μl/well of AffiniPure Goat anti-Human IgG Fcγ fragment (cat. no. 109-005-098, Jackson Immunoresearch, West Grove, Pa.) or specific antigen at 10 μg/ml in PBS and incubated overnight at 4° C. Before use, coating solutions were removed and washed 3× with PBS, 0.05 % Tween 20, then blocked for at least 1 hr. with 200 μl/well PBS, 0.05% Tween 20, 1% BSA (PBST/BSA). Blocking solutions were removed and the samples were analyzed against a standard curve. Both the standard and unknowns were typically diluted in PBST/BSA, incubated for 2 hr. at room temperature, and then washed as described above. An aliquot of 50 µl/well of peroxidase conjugated AffiniPure Donkey anti-Human IgG (H+L) (Jackson Immunoresearch cat. no. 709-035-149) was used to detect the presence of antibody. The conjugate was diluted 1:10,000 in PBST/BSA and incubated for 1.5 hr at room temperature, then removed and washed as above. An aliquot of 100 µl/well of substrate (420 mM tetramethyl benzidine and 0.05% hydrogen peroxide in 0.1 M sodium acetate buffer pH 4.9) was then added to resolve bound antigen by incubation with substrate for 2 min, followed by fixation with a stop buffer of 100 µl/well 2 N sulfuric acid. Resultant absorbance was read at 450 nm on a Molecular Devices SpectraMax Plus plate reader using the Softmax software (Molecular Devices, Sunnyvale, Calif.).

For the FRET assay, 50 µL of conditioned media samples were mixed with 75 µL of 1.67 µg/mL Lance™ Eu-IDEC-152 (an IgG1 monoclonal antibody labeled with europium) Perkin Elmer (Boston, Mass.) diluted in PBS with 1% BSA (Dulbecco's Phosphate Buffered Saline Solution, cat. no. 9280, Irvine Scientific, Santa Ana, Calif.; BSA, Sigma, cat. no. CA-7906). After the addition of the labeled antibody, 75 uL of assay mix is added containing 6.67 µg/mL PhycolinkR-Goat Anti-human IgG (Fc specific)-XL Allophycocyanin (APC) Conjugate (cat. no. PJ253, Prozyme San Leandro, Calif.) diluted in PBS with 1% BSA. Samples plus mix were incubated in Full well Non-Treat 96 Well Black Plate with lids, (cat. no. 237105, NalgeNunc International, Rochester, N.Y.) and agitated for greater than 15 minutes using a Titer Plate Shaker, (cat. no. 4625 (VWR# 57019-600), Barnstead/Lab-Line, Melrose Park, Ill.). Plates are read using a 1420 Multilabel Counter (Wallac, Gaithersburg, Md.) in a time resolved fluorescence mode with excitation at 337 nM and emission at 665 nM. Data was analyzed using Softmax software (Molecular Devices).

EXAMPLES

Example 1

Methods for Engineering a Vector for Expressing Multiple Polypeptides Using Alternative Splicing The following example describes methods for constructing a vector suitable for expressing in eukaryotic cells, two or more gene products by alternative splicing.

The expression vectors described herein are derivatives of the expression vector pV80 described in U.S. application Ser. No. 10/545,420, which contains a native CMV intron with the native CMV splice donor and splice acceptor. Briefly, a DNA construct was made comprising (in a 5' to 3' or downstream direction) a cytomegalovirus immediate early 1 (CMV IE1) promoter including the 5' untranslated region that precedes the CMV IE1 intron (human cytomegalovirus strain AD169) and the 5' half of the CMV IE1 intron, including the native splice donor sequence (SD). The modified 3' portion of the CMV IE1 intron included a cloning polylinker (SwaI-BstBI) for alternative splice acceptors (SA1) to be conveniently exchanged. In addition, a cloning site (AscI) for the first coding sequence, into which a humanized light chain gene was cloned was added just downstream of SA1 along with a variant human growth hormone (hGH) polyadenylation region. Still further downstream, the 3' portion of the CMV IE1 intron, including the native splice acceptor (SA2) sequence, was incorporated into the vector. A cloning site (BamHI) for the second coding sequence, into which a humanized IgG1 heavy chain gene was cloned was added just downstream of SA2 along with the variant human growth hormone (hGH) polyadenylation region. At a separate location in the vector, the dihydrofolate reductase (DHFR) selectable marker was introduced. The selectable marker is derived from pSI (Genbank accession # U47121, Promega, Madison, Wis.) and is transcriptionally controlled by the SV40 promoter/enhancer, an artificial intron (separate from the alternative splicing vector) and the SV40 late polyadenylation sequence. For cloning and propagating the alternative splicing vector in prokaryotic cells, sequences derived from pUC19 that include the beta lactamase gene were added.

The resultant vector (i.e., pHL005) from the foregoing engineering steps is shown in FIG. 3 (see also SEQ ID NO: 29 which provides the vector backbone sequence without the exon coding sequences inserted into the AscI and BamHI sites). In this example, humanized antibody light and heavy chain sequences have been cloned into the AscI and BamHI sites, respectively. This vector also allows for the insertion of a variety of splice acceptors at restriction sites (SwaI-BstBI) just upstream of the first coding sequence to, optionally, change the ratio of light and heavy chain expression.

Additional expression vectors were made where portions of the intron just 5' of the splice acceptor were deleted to generate the vector backbone of pHLP005. The intron sequence of pHLP005 contains a PflMI site and a BspEI site approximately 310 base pairs and 110 base pairs 5' of a SwaI site, respectively. To generate these deletions the pHLP005 plasmid was linearized by partial digestion with either PflMI or BspEI and then completely digested with BspEI and gel purified.

To generate the expression vectors with different first splice acceptors (SA1), oligo-nucleotides with PflMI and BspEI or BspEI and BspEI compatible sites (SEQ ID NOs: 1-28) were ligated into the respective pHLP005 digested vector and given a new vector designation (FIG. 4). All constructs were then confirmed by DNA sequence analysis The resulting vectors contain, in 5' to 3' or downstream orientation, a native CMV splice donor (SD), a first splice acceptor (SA1) selected from SEQ ID NOs:1-28, a first restriction site (AscI) for the insertion of the first polypeptide, a second splice acceptor (SA2) which is a native CMV splice acceptor, and a second restriction site (BamHI) for the introduction of the second polypeptide The antibody light and heavy chain sequences were prepared using primer based polymerase chain reaction (PCR) and the resultant products were introduced into the vector using standard genetic engineering techniques. The primers used contained restriction sites adjacent to the coding regions for insertion into the AscI and BamHI sites. For example the 5' primer could be TTTTGGCGCGCCATGN(20) (SEQ ID NO: 32) for the light chain and TTTTGGATCCATGN(20) (SEQ ID NO: 33) for the heavy chain. The 3' primer could be GCACGGCGCGCCCTAN(20) (SEQ ID NO: 34) for the light chain and GCAGGGATCCTCAN(20) (SEQ ID NO: 35) for the heavy chain. For these primers, N(20) represents the nucleotide sequence specific for the DNA encoding the desired heavy or light chain.

Example 2

Methods for Determining Alternative Splicing Efficiency

In this example, methods and constructs for determining the efficiency of using alternative splicing to express two different gene products encoded by exons adjacent to different splice acceptors are described.

Although splicing is mediated by the consensus sequences at the exon/intron junctions, an accurate prediction of splicing efficacy cannot be determined by these sequences alone. For this reason an empirical approach is necessary to identify splice acceptor sequences that would generate the appropriate ratio of products, which can be measured here as the total amount of multimeric protein produced. Accordingly, the invention provides convenient vectors for efficiently screening combinations of desirable splice sites in any given cell line.

To generate a variety of expression vectors with alternative splice sites, oligonucleotides were generated with a blunt end and a BstBI compatible end for insertion into the SwaI and BstBI sites in the pHLP005 vector. All constructs were confirmed by DNA sequence analysis. The sequences of the splice sites tested are provided in FIG. 4 and in the sequence listing (i.e., SEQ ID NOS: 1-28).

The vectors generated with the various splice acceptors were compared using transient or stable transfection by electroporation. The host cell used for transfections was the dihydrofolate reductase (DHFR) deficient Chinese hamster ovary (CHO) cell line DG44 (Urlaub et al., Cell 33, 405-412 (1983)). All DNA was prepared using the Megaprep kit (Qiagen, Valencia, Calif.). Prior to transfection, DNA was ethanol (EtOH) precipitated, washed in 70% EtOH, dried, resuspended in HEBS, and quantitated prior to transfection. Negative controls contained no DNA transfection and were used as transfection controls. Both the mAb specific ELISA and the IgG specific ELISA measure the total antibody secreted into the cell culture medium. Total antibody expression levels for the transiently transfected cells are provided in Table 1.

Results demonstrate that certain splice sites, e.g. pHLP0015 and pHLP0018, are more efficient than others, generating higher levels of total antibody, when tested, transiently, in CHO cells.

TABLE 1

Antibody Titers from Transient Transfection

| Plasmid(s) | Titer using the mAb specific ELISA (ng/ml) | Titer using the IgG specific ELISA (ng/ml) |
|---|---|---|
| HC + LC | 1265.8 | 1313.8 |
| HC + LC | 1418.6 | 1262.5 |
| pHLP006 | 11.8 | 12.9 |
| pHLP006 | 11.4 | 7.6 |
| pHLP015 | 141.6 | 153 |
| pHLP015 | 129.4 | 143.8 |
| pHLP017 | 34.7 | 27.7 |
| pHLP017 | 33.5 | 26.1 |
| pHLP018 | 204.7 | 227.1 |
| pHLP018 | 253.9 | 271.3 |
| pHLP019 | 26.3 | 18.4 |
| pHLP019 | 25.8 | 17.1 |
| pHLP020 | 53 | 41.7 |
| pHLP020 | 53.5 | 39.2 |
| no DNA | 0 | 0 |
| no DNA | 0 | 0 |

Example 3

Expression of Alternatively Spliced Gene Products in Eukaryotic Cells

In this example, the expression of alternatively spliced gene products, in particular, assembled IgG antibodies, is described.

Briefly, CHO cells were transfected with the alternative splicing vectors of the invention by electroporation and allowed to recover in selective media, as described supra, for about two weeks to generate stably transfected cells. After 3-5 days conditioned media was harvested and the antibody titer was determined by ELISA.

In a first experiment, 50 µg of DNA of separate vectors encoding antibody light and heavy chain, 50 µg of alternatively spliced vectors encoding both antibody light and heavy chains, or no DNA at all was introduced into eukaryotic cells (CHO) and the amount of functional polypeptide multimers produced by the cells as a function of antibody binding activity was determined (Table 2).

TABLE 2

Specific Productivity of Stable Pools

| Plasmid(s) | Integral Cell Area (cell days/ml) | Titer using the IgG specific ELISA (ng/ml) | Titer using the mAb specific ELISA (ng/ml) | Specific productivity using the IgG specific ELISA (pg/cell day) | Specific productivity using the mAb specific ELISA (pg/cell day) |
|---|---|---|---|---|---|
| pKJS195 (LC) pKJS189 (HC) | 9.28E+05 | 241 | 218 | 0.260 | 0.235 |
| pKJS195 (LC) pKJS189 (HC) | 9.25E+05 | 290 | 243 | 0.313 | 0.263 |
| pHLP005 | 1.32E+06 | 58 | 39 | 0.044 | 0.030 |
| pHLP005 | 1.07E+06 | 43 | 25 | 0.040 | 0.023 |
| pHLP006 | 1.17E+06 | 37 | 36 | 0.032 | 0.031 |
| pHLP006 | 1.05E+06 | 26 | 23 | 0.025 | 0.022 |
| pHLP010 | 1.01E+06 | 29 | 31 | 0.029 | 0.031 |
| pHLP010 | 9.52E+05 | 33 | 28 | 0.035 | 0.029 |

Results from the first experiment are proof of principle that it is possible to generate a functional polypeptide multimer, e.g., a monoclonal antibody product, from an alternative splicing vector.

In additional experiments, 25 µg of DNA of separate vectors encoding antibody light and heavy chain, 50 µg of alternatively spliced vectors encoding both antibody light and heavy chains, or no DNA at all was introduced into eukaryotic cells (CHO) and the amount of functional polypeptide multimers produced by the cells as a function of antibody binding activity, was determined (Tables 3-6).

Results from the experiments demonstrate that it is possible to generate a functional polypeptide multimer, e.g., a monoclonal antibody product, from an alternative splicing vector. The data suggest that pHLP015 is a better alternative splicing vector than others tested because of its ability to produce high levels of functional antibody.

TABLE 3

Antibody Titers from Transient Transfection

| Plasmid(s) | Titer using the mAb specific ELISA (ng/ml) | Titer using the IgG specific ELISA (ng/ml) |
|---|---|---|
| pKJS195 (LC) pKJS189 (HC) | 464 | 451 |
| pKJS195 (LC) pKJS189 (HC) | 493 | 483 |
| pHLP006 | 3.4 | 1.1 |
| pHLP006 | 3.1 | 0.5 |
| pHLP007 | 10.5 | 7.8 |
| pHLP007 | 11.6 | 12.8 |
| pHLP010 | 3.6 | 3.1 |
| pHLP010 | 3.3 | 3 |
| pHLP011 | 16.4 | 13.4 |
| pHLP011 | 14 | 12.3 |

TABLE 3-continued

Antibody Titers from Transient Transfection

| Plasmid(s) | Titer using the mAb specific ELISA (ng/ml) | Titer using the IgG specific ELISA (ng/ml) |
|---|---|---|
| pHLP012 | 18.1 | 16 |
| pHLP012 | 11.8 | 11.1 |
| pHLP013 | 0 | 7 |
| pHLP013 | 0 | 6.5 |
| pHLP014 | 14.1 | 10.7 |
| pHLP014 | 7.9 | 6.6 |
| pHLP015 | 66.6 | 78.8 |
| pHLP015 | 62.8 | 71.4 |
| pHLP016 | 10.1 | 7.3 |
| pHLP016 | 10.3 | 9 |
| no DNA | 0 | 0 |
| no DNA | 0 | 0 |

TABLE 4

Specific Productivity of Stable Pools

| Plasmid(s) | Integral Cell Area (cell days/ml) | Titer using the mAb specific ELISA (ng/ml) | Specific productivity using the mAb specific ELISA (pg/cell day) |
|---|---|---|---|
| pKJS195 (LC) pKJS189 (HC) | 1.64E+06 | 338 | 0.21 |
| pKJS195 (LC) pKJS189 (HC) | 1.87E+06 | 377 | 0.20 |
| pHLP015 | 1.72E+06 | 130 | 0.08 |
| pHLP015 | 1.75E+06 | 151 | 0.09 |

TABLE 5

Antibody Titers from Transient Transfection

| Plasmid(s) | Titer using the mAb specific ELISA (ng/ml) |
|---|---|
| pKJS195 (LC) pKJS189 (HC) | 1005 |
| pKJS195 (LC) pKJS189 (HC) | 1015 |
| pHLP006 | 7.6 |
| pHLP006 | 6.9 |
| pHLP015 | 100.5 |
| pHLP015 | 88.6 |
| pHLP017 | 17.3 |
| pHLP017 | 23.4 |
| pHLP018 | 142.2 |
| pHLP018 | 185.5 |
| pHLP019 | 19 |
| pHLP019 | 17 |
| pHLP020 | 40 |
| pHLP020 | 38 |
| no DNA | 0 |
| no DNA | 0 |

TABLE 6

Specific Productivity of Stable Pools

| Plasmid(s) | Integral Cell Area (cell days/ml) | Titer using the mAb specific ELISA (ng/ml) | Titer using the IgG specific ELISA (ng/ml) | Specific productivity using the mAb specific ELISA (pg/cell day) | Specific productivity using the IgG specific ELISA (pg/cell day) |
|---|---|---|---|---|---|
| pKJS195 (LC) pKJS189 (HC) | 1.37E+06 | 341.1 | 362.8 | 0.25 | 0.27 |
| pKJS195 (LC) pKJS189 (HC) | 1.49E+06 | 374.5 | 395.6 | 0.25 | 0.27 |
| pHLP006 | 1.38E+06 | 42.2 | 31.6 | 0.03 | 0.02 |
| pHLP015 | 1.25E+06 | 229.7 | 196.1 | 0.18 | 0.16 |
| pHLP015 | 1.02E+06 | 169.4 | 166.4 | 0.17 | 0.16 |
| pHLP017 | 1.70E+06 | 42.2 | 30.2 | 0.02 | 0.02 |
| pHLP017 | 1.22E+06 | 32.6 | 23.4 | 0.03 | 0.02 |
| pHLP018 | 1.43E+06 | 194.2 | 173.1 | 0.14 | 0.12 |
| pHLP018 | 1.21E+06 | 178.8 | 140.3 | 0.15 | 0.12 |
| pHLP019 | 1.29E+06 | 35.9 | 24.6 | 0.03 | 0.02 |
| pHLP019 | 1.16E+06 | 31.7 | 22 | 0.03 | 0.02 |
| pHLP020 | 1.32E+06 | 45.5 | 30.7 | 0.03 | 0.02 |
| pHLP020 | 1.42E+06 | 43.9 | 29.2 | 0.03 | 0.02 |

Accordingly, it was concluded that a functional polypeptide multimer, e.g., an antibody, can be produced using an alternative splicing vector both transiently and stably in eukaryotic cells. Therefore, the ease and utility of a one vector system expressing more than one polypeptide through alternative splicing was demonstrated.

Example 4

Demonstration that the Vector can Produce Cell Lines with Good Expression Potential The vector of the present invention was designed to optimize the ratio of light and heavy chains for antibody expression. Immunoglobulin heavy chains are not secreted unless assembled with light chains, while most light chains can be secreted as free molecules. Thus, excessive amounts of free light chain would be indicative of the need to further optimize the vector to increase the ratio of heavy to light chain production. In order to evaluate the production of free light chain, cell lines containing one of the vectors of the invention were generated and their conditioned media, containing the secreted recombinant free light chain and/or assembled antibody multimer products, was evaluated (Table 7).

Vector Generation

A pHLP015-based vector was prepared as described in Examples 1 and 2. This vector was inserted into CHO cells and selected for stable transfection as described previously. Amplified cell lines were derived with targeting the industry-standard of a specific productivity in excess of 10 picograms of protein produced per cell per day as measured by FRET analysis as described previously. The results provided below demonstrate the usefulness of this expression vector in making cell lines acceptable for antibody production.

RT-PCR Results Confirm Predicted Splice Sites

Reverse transcription of cellular RNA followed by polymerase chain reaction of the cDNA (RT-PCR) was performed to confirm the splice junctions for the light and heavy chain mRNAs against the junctions predicted from the expression vector design. A stably transfected cell line was isolated from one of the transfections using the plasmid pHLP015 and total RNA was prepared (RNAwiz, Ambion, Austin, Tex.). Using a primer complementary to the approximate center of the heavy chain mRNA, a cDNA was generated using reverse transcriptase (Superscript III reverse tranrciptase, Invitrogen, Carlsbad, Calif.). The cDNA was then used as a template for PCR (Vent DNA polymerase, New England Biolabs, Beverly, Mass.) using a primer in the CMV 5' untranslated region (5' of the splice donor) and a primer in the coding region (3' of the splice acceptor in the heavy chain coding sequence). This PCR product was sequenced and the predicted splice product between the splice donor in the CMV intron and the splice acceptor just 5' of the heavy chain coding sequence was confirmed.

Using oligo(dT)15 as a primer, a cDNA was generated from the cellular RNA using reverse transcriptase (Reverse transcription system, Promega, Madison, Wis.). This cDNA was then used as a template for PCR (Vent DNA polymerase, New England Biolabs, Beverly, Mass.) using a primer in the CMV 5' untranslated region (5' of the splice donor) and a primer in the coding region (3' of the splice acceptor in the light chain coding sequence). This PCR product was sequenced and the predicted splice product between the splice donor in the CMV intron and the splice acceptor just 5' of the light chain coding sequence was confirmed indicating that the expression vector was functioning by alternative splicing as expected.

SDS-PAGE Analysis of Conditioned Media

A stably transfected cell line was isolated from a transfection using the plasmid pHLP015 (mAb#1-1 in Table 7) from Examples 1-3. In addition, a number of stably transfected cell lines were generated using another pHLP015-based vector (as generated in this Example, mAb#2-1 to 5 in Table 7).

To purify both the whole mAb and free light chains, approximately 50 mL of conditioned medium was applied to a 1.3 mL column of protein L-agarose (cat. no. P3351, Sigma-Aldrich, St. Louis, Mo.), the column washed with 15 mL 3×PBS, then 5 mL 1×PBS and eluted with 100 mM $NaH_2PO_4$, pH 2.8 in 0.3 mL aliquots and neutralized immediately with 75 µL 1 M Hepes, pH 8. The protein peak was located by UV absorbance at 280 nm and the protein concentration determined using an extinction coefficient of 1.5 A280/mg/mL. An appropriate volume of the peak sample was diluted into sample buffer to load 1.5 µg protein in 15 µL.

The 4× stock solution of Laemmli-based sample buffer (0.25 M Tris-HCl, pH 6.8, 8% SDS, 40% glycerol, and 0.01% bromophenol blue) was prepared with fresh 100 mM NEM for non-reducing gels. The samples were heated for 5 min at 100° C. and 15 µL loaded onto PAGEr Gold Precast 4-20% tris-glycine gels (cat. no. 59517, Cambrex, East Rutherford, N.J.). The gels were run at 45 mA for 40 min in Laemmli buffer. After the run the gels were stained with approximately 100 mL Coomassie Blue Cleveland Stain (50% methanol, 10% acetic acid, 0.1% Coomassie blue) by microwaving for 1 min and shaking 10 min. The gels were then destained in approximately 100 mL 10% methanol, 10% acetic acid by microwaving for 2 min and shaking overnight with absorbent foam. Gels were scanned on a Biorad GS-800 Calibrated Densitometer and the whole antibody and free light chain bands quantified with Biorad Quantity One software. The amount of free light chain as a percentage of the total secreted protein (whole antibody+free light chain) is shown in Table 7.

TABLE 7

Evaluation of the Relative Amounts of Whole Antibody and Free Light Chain in Conditioned Media from pHLP015 Based Cell Lines

| Cell line | % free LC |
|---|---|
| mAb#1-1 | none detected |
| mAb#2-1 | 14 |
| mAb#2-2 | 14 |
| mAb#2-3 | 16 |
| mAb#2-4 | none detected |
| mAb#2-5 | none detected |

As shown in Table 7, high levels of free light chain were not detected indicating that the vector is well balanced in the expression of light chain relative to heavy chain.

Example 5

Vectors Producing Multimeric Proteins

The vectors and expression cassettes or constructs of the present invention can be used to express any multimeric protein, including, but not limited to, the multimeric proteins described in the Detailed Description supra. Many such proteins are well known in the art and are suitable for use in the vectors and expression cassettes or constructs of the present invention. The number of polypeptides to be expressed can vary. For example, two polypeptides can be expressed as described previously. Additional polypeptides can be expressed by inserting further exons encoding the polypeptides into the vector, preferably between the first exon and second splice acceptor. Each of the additional exons would have a splice acceptor 5' to the exon to regulate transcription as splicing occurs between the single splice donor and the individual splice acceptors. Thus, more than one polypeptide can be expressed using the same splice donor and different splice acceptors to express the polypeptides in ratios to optimize the expression of the desired protein or proteins.

A vector or expression cassette or construct is prepared as described in the foregoing examples that contains splice acceptors that allow splicing and subsequent translation of the polypeptide chains in ratios that optimize the expression of the multimeric protein. First, the genes encoding the polypeptide chains are cloned or amplified using standard techniques, such as RT-PCR using primers specific for the chains and an appropriate library containing the genes expressing the desired polypeptides. The genes are then inserted into a vector or expression cassette or construct of the invention capable of expressing the polypeptides in the proper ratios sufficient to express high levels of the multimeric protein. This vector or expression cassette or construct can have convenient restriction sites to facilitate the insertion of the splice sites, exons and other desired elements. For example, pHLP0015 can be used. Alternatively, the genes encoding the polypeptides are inserted into more than one vector or expression cassette or construct, each with a different first splice acceptor, to screen for a splice acceptor that allows for the proper expression level, as described in Examples 2 and 3. Finally, the vector or vectors or expression cassettes or constructs encoding the polypeptides are inserted into an appropriate cell line, e.g. mammalian cells, insect cells or yeast cells, and expressed. The multimeric protein can then be collected from the cell culture medium if secreted, or from the lysed cells if the protein is intracellular or membrane-bound.

All references cited herein are hereby incorporated by reference in their entirety.

Equivalents

For one of ordinary skill in the art, using no more than routine experimentation, there are many equivalents to the specific embodiments of the invention described herein. Such equivalents are intended to be encompassed by the following claims.

What is claimed is:

1. An expression vector comprising,
   a promoter;
   a 5' UTR;
   a single splice donor;
   an intron;
   a first splice acceptor;
   a first exon encoding a first polypeptide;
   a second splice acceptor; and
   a second exon encoding a second polypeptide,
   wherein the promoter is operably linked to the first and second exon,
   wherein upon entry into a cell, said single splice donor splices with said first splice acceptor, forming a spliced transcript which permits translation of said first exon, and said second splice acceptor forming a spliced transcript which permits translation of said second exon,
   wherein said first or second splice acceptor, or both, comprise any one of the sequences selected from the group consisting of SEQ ID NOS: 1-28, and
   wherein said first polypeptide and said second polypeptide are expressed from said spliced transcripts.

2. The vector of claim 1, wherein the promoter is a CMV promoter.

3. The vector of claim 1, further comprising a polyadenylation signal operably linked to said first exon or second exon.

4. The vector of claim 1, wherein said vector further comprises one or more additional splice acceptor and additional exon encoding an additional polypeptide,
   wherein said one or more additional splice acceptor comprises any one of the sequences selected from the group consisting of SEQ ID NOS: 1-28, and
   wherein upon entry into a cell, said single splice donor splices with said additional splice acceptor, forming an additional spliced transcript which permits translation of said additional exon, and
   wherein said additional polypeptide is expressed from said additional spliced transcript.

5. The vector of claim 1, wherein said first or second exons or both encode a selectable marker.

6. The vector of claim 1, wherein said first and second polypeptide form a multimer.

7. The vector of claim 6, wherein said multimeric protein is a heterodimer, a heterotrimer, or a heterotetramer.

8. The vector of claim 1, wherein said splice donor and said second splice acceptor are derived from CMV and said first splice acceptor comprises any one of the sequences selected from the group consisting of SEQ ID NOS: 1-28.

9. The vector of claim 1, wherein said vector is a viral vector.

10. The vector of claim 1 comprising SEQ ID NO: 29.

11. An isolated eukaryotic cell containing the vector of claim 1.

12. The isolated cell of claim 11, wherein the vector is integrated into the chromosomal DNA of said cell.

13. The isolated cell of claim 11, wherein the vector is episomal.

14. The isolated cell of claim 11, wherein said cell is a mammalian cell or a yeast cell.

15. The cell of claim 14, wherein said cell is selected from the group comprising: a baby hamster kidney cell, a fibroblast, a myeloma cell, an NS0 cell, a PER.C6 cell, or a Chinese Hamster Ovary (CHO) cell.

16. The cell of claim 15, wherein said cell is a Chinese Hamster Ovary (CHO) cell.

17. A method of producing polypeptides, the method comprising:
 (a) culturing a cell of claim 11 in a culture; and,
 (b) isolating said first polypeptide and said second polypeptide from the culture.

18. An expression vector comprising,
a promoter;
a 5' UTR;
a single splice donor;
an intron;
a first splice acceptor;
a first exon encoding a first antibody polypeptide or fragment thereof
a second splice acceptor; and
a second exon encoding a second antibody polypeptide or fragment thereof,
wherein the promoter is operably linked to the first and second exon,
wherein upon entry into a cell, said single splice donor splices with said first splice acceptor, forming a spliced transcript which permits translation of said first exon, and said second splice acceptor, forming a spliced transcript which permits translation of said second exon,
wherein said first or said second splice acceptor, or both, comprise any one of the sequences selected from the group consisting of SEQ ID NOS: 1-28, and
wherein said first antibody polypeptide or fragment thereof and said second antibody polypeptide or fragment thereof are expressed from said spliced transcripts and associate to form an antibody or antibody fragment.

19. The vector of claim 18, wherein said first exon or said second exon or both encode an antibody fragment.

20. The vector of claim 18, wherein said first polypeptide is an antibody heavy chain or a fragment thereof and said second polyp eptide is an antibody light chain or a fragment thereof.

21. The vector of claim 18, wherein said first polypeptide is an antibody light chain or a fragment thereof and said second polyp eptide is an antibody heavy chain or a fragment thereof.

22. The vector of claim 20, wherein the light or heavy chain or both is murine, chimeric, humanized, human or synthetic.

23. The vector of claim 21, wherein the light or heavy chain or both is murine, chimeric, humanized, human or synthetic.

24. The vector of claim 18, wherein said splice donor and said second splice acceptor are derived from CMV and said first splice acceptor comprises any one of the sequences selected from the group consisting of SEQ ID NOS: 1-28.

25. The vector of claim 18, wherein said vector is a viral vector.

26. The vector of claim 18, comprising SEQ ID NO: 29.

27. An isolated eukaryotic cell containing the vector of claim 18.

28. The isolated cell of claim 27, wherein said vector is integrated into the chromosomal DNA of said cell.

29. The isolated cell of claim 27, wherein said vector is episomal.

30. The isolated cell of claim 27, wherein said cell is a mammalian cell or a yeast cell.

31. The cell of claim 30, wherein said cell is selected from the group comprising: a baby hamster kidney cell, a fibroblast, a myeloma cell, an NS0 cell, a PER.C6 cell, or a Chinese Hamster Ovary (CHO) cell.

32. The cell of claim 31, wherein said cell is a Chinese Hamster Ovary (CHO) cell.

33. A method of producing antibodies or antibody fragments, the method comprising:
 (a) culturing a cell of claim 27 in a culture; and,
 (b) isolating said first antibody polypeptide or fragment thereof and said second antibody polypeptide or fragment thereof from the culture.

* * * * *

SEQUENCE LISTING

<160> NUMBER OF SEQ ID NOS: 35

<210> SEQ ID NO 1
<211> LENGTH: 22
<212> TYPE: DNA
<213> ORGANISM: Artificial Sequence
<220> FEATURE:
<223> OTHER INFORMATION: Splice site cassette

<400> SEQUENCE: 1
aaatctgcag tcttcgaaca gg                                              22

<210> SEQ ID NO 2
<211> LENGTH: 22
<212> TYPE: DNA
<213> ORGANISM: Artificial Sequence
<220> FEATURE:
<223> OTHER INFORMATION: Splice site cassette

<400> SEQUENCE: 2
tttagacgtc agaagcttgt cc                                              22

<210> SEQ ID NO 3
<211> LENGTH: 21
<212> TYPE: DNA
<213> ORGANISM: Artificial Sequence
<220> FEATURE:
<223> OTHER INFORMATION: Splice site cassette

<400> SEQUENCE: 3
aattctgcag tcaccgtcct t                                               21

<210> SEQ ID NO 4
<211> LENGTH: 23
<212> TYPE: DNA
<213> ORGANISM: Artificial Sequence
<220> FEATURE:
<223> OTHER INFORMATION: Splice site cassette

<400> SEQUENCE: 4
ttaagacgtg agtggcagga agc                                             23

<210> SEQ ID NO 5
<211> LENGTH: 21
<212> TYPE: DNA
<213> ORGANISM: Artificial Sequence
<220> FEATURE:
<223> OTHER INFORMATION: Splice site cassette

<400> SEQUENCE: 5
aattctgcac tcaccgtcct t                                               21

<210> SEQ ID NO 6
<211> LENGTH: 23
<212> TYPE: DNA
<213> ORGANISM: Artificial Sequence
<220> FEATURE:
<223> OTHER INFORMATION: Splice site cassette

<400> SEQUENCE: 6
ttaagacgtg agtggcagga agc                                             23

<210> SEQ ID NO 7
<211> LENGTH: 21

```
<212> TYPE: DNA
<213> ORGANISM: Artificial Sequence
<220> FEATURE:
<223> OTHER INFORMATION: Splice site cassette

<400> SEQUENCE: 7
aattgtgcag tcaccgtcct t                                              21

<210> SEQ ID NO 8
<211> LENGTH: 23
<212> TYPE: DNA
<213> ORGANISM: Artificial Sequence
<220> FEATURE:
<223> OTHER INFORMATION: Splice site cassette

<400> SEQUENCE: 8
ttaacacgtc agtggcagga agc                                            23

<210> SEQ ID NO 9
<211> LENGTH: 21
<212> TYPE: DNA
<213> ORGANISM: Artificial Sequence
<220> FEATURE:
<223> OTHER INFORMATION: Splice site cassette

<400> SEQUENCE: 9
aattctgcaa tcaccgtcct t                                              21

<210> SEQ ID NO 10
<211> LENGTH: 23
<212> TYPE: DNA
<213> ORGANISM: Artificial Sequence
<220> FEATURE:
<223> OTHER INFORMATION: Splice site cassette

<400> SEQUENCE: 10
ttaagacgtt agtggcagga agc                                            23

<210> SEQ ID NO 11
<211> LENGTH: 21
<212> TYPE: DNA
<213> ORGANISM: Artificial Sequence
<220> FEATURE:
<223> OTHER INFORMATION: Splice site cassette

<400> SEQUENCE: 11
aagctagcag tcaccgtcct t                                              21

<210> SEQ ID NO 12
<211> LENGTH: 23
<212> TYPE: DNA
<213> ORGANISM: Artificial Sequence
<220> FEATURE:
<223> OTHER INFORMATION: Splice site cassette

<400> SEQUENCE: 12
ttcgatcgtc agtggcagga agc                                            23

<210> SEQ ID NO 13
<211> LENGTH: 21
<212> TYPE: DNA
<213> ORGANISM: Artificial Sequence
<220> FEATURE:
<223> OTHER INFORMATION: Splice site cassette

<400> SEQUENCE: 13
```

-continued

```
aattctgcgg tcaccgtcct t                                              21

<210> SEQ ID NO 14
<211> LENGTH: 23
<212> TYPE: DNA
<213> ORGANISM: Artificial Sequence
<220> FEATURE:
<223> OTHER INFORMATION: Splice site cassette

<400> SEQUENCE: 14
ttaagacgcc agtggcagga agc                                            23

<210> SEQ ID NO 15
<211> LENGTH: 21
<212> TYPE: DNA
<213> ORGANISM: Artificial Sequence
<220> FEATURE:
<223> OTHER INFORMATION: Splice site cassette

<400> SEQUENCE: 15
aagaggcctc tcaccgtcct t                                              21

<210> SEQ ID NO 16
<211> LENGTH: 23
<212> TYPE: DNA
<213> ORGANISM: Artificial Sequence
<220> FEATURE:
<223> OTHER INFORMATION: Splice site cassette

<400> SEQUENCE: 16
ttctccggag agtggcagga agc                                            23

<210> SEQ ID NO 17
<211> LENGTH: 21
<212> TYPE: DNA
<213> ORGANISM: Artificial Sequence
<220> FEATURE:
<223> OTHER INFORMATION: Splice site cassette

<400> SEQUENCE: 17 aaggggcag tcaccgtcct t                                               21

<210> SEQ ID NO 18
<211> LENGTH: 23
<212> TYPE: DNA
<213> ORGANISM: Artificial Sequence
<220> FEATURE:
<223> OTHER INFORMATION: Splice site cassette

<400> SEQUENCE: 18
ttcccccgtc agtggcagga agc                                            23

<210> SEQ ID NO 19
<211> LENGTH: 21
<212> TYPE: DNA
<213> ORGANISM: Artificial Sequence
<220> FEATURE:
<223> OTHER INFORMATION: Splice site cassette

<400> SEQUENCE: 19
aagctagcag tcgaccacct t                                              21

<210> SEQ ID NO 20
<211> LENGTH: 23
<212> TYPE: DNA
<213> ORGANISM: Artificial Sequence
```

```
<220> FEATURE:
<223> OTHER INFORMATION: Splice site cassette

<400> SEQUENCE: 20
ttcgatcgtc agctggtgga agc                                              23

<210> SEQ ID NO 21
<211> LENGTH: 24
<212> TYPE: DNA
<213> ORGANISM: Artificial Sequence
<220> FEATURE:
<223> OTHER INFORMATION: Splice site cassette

<400> SEQUENCE: 21
ccggaggggg cagtcaccgt cctt                                             24

<210> SEQ ID NO 22
<211> LENGTH: 22
<212> TYPE: DNA
<213> ORGANISM: Artificial Sequence
<220> FEATURE:
<223> OTHER INFORMATION: Splice site cassette

<400> SEQUENCE: 22
tcccccgtca gtggcaggaa gc                                               22

<210> SEQ ID NO 23
<211> LENGTH: 23
<212> TYPE: DNA
<213> ORGANISM: Artificial Sequence
<220> FEATURE:
<223> OTHER INFORMATION: Splice site cassette

<400> SEQUENCE: 23
atgggggggc agtcaccgtc ctt                                              23

<210> SEQ ID NO 24
<211> LENGTH: 28
<212> TYPE: DNA
<213> ORGANISM: Artificial Sequence
<220> FEATURE:
<223> OTHER INFORMATION: Splice site cassette

<400> SEQUENCE: 24 ttgtacccccc ccgtcagtgg caggaagc                                        28

<210> SEQ ID NO 25
<211> LENGTH: 24
<212> TYPE: DNA
<213> ORGANISM: Artificial Sequence
<220> FEATURE:
<223> OTHER INFORMATION: Splice site cassette

<400> SEQUENCE: 25
ccggattctg cagtcaccgt cctt                                             24

<210> SEQ ID NO 26
<211> LENGTH: 22
<212> TYPE: DNA
<213> ORGANISM: Artificial Sequence
<220> FEATURE:
<223> OTHER INFORMATION: Splice site cassette

<400> SEQUENCE: 26
taagacgtca gtggcaggaa gc                                               22
```

<210> SEQ ID NO 27
<211> LENGTH: 23
<212> TYPE: DNA
<213> ORGANISM: Artificial Sequence
<220> FEATURE:
<223> OTHER INFORMATION: Splice site cassette

<400> SEQUENCE: 27
atggttctgc agtcaccgtc ctt                                    23

<210> SEQ ID NO 28
<211> LENGTH: 28
<212> TYPE: DNA
<213> ORGANISM: Artificial Sequence
<220> FEATURE:
<223> OTHER INFORMATION: Splice site cassette

<400> SEQUENCE: 28
ttgtaccaag acgtcagtgg caggaagc                               28

<210> SEQ ID NO 29
<211> LENGTH: 6801
<212> TYPE: DNA
<213> ORGANISM: Artificial Sequence
<220> FEATURE:
<223> OTHER INFORMATION: Artificial Vector

<400> SEQUENCE: 29
agcttgacat tgattattga ctagttatta atagtaatca attacggggt cattagttca      60
tagcccatat atggagttcc gcgttacata acttacggta aatggcccgc ctggctgacc     120
gcccaacgac ccccgcccat tgacgtcaat aatgacgtat gttcccatag taacgccaat     180
agggactttc cattgacgtc aatgggtgga gtatttacgg taaactgccc acttggcagt     240
acatcaagtg tatcatatgc caagtacgcc ccctattgac gtcaatgacg gtaaatggcc     300
cgcctggcat tatgcccagt acatgacctt atgggacttt cctacttggc agtacatcta     360
cgtattagtc atcgctatta ccatggtgat gcggttttgg cagtacatca atgggcgtgg     420
atagcggttt gactcacggg gatttccaag tctccacccc attgacgtca atgggagttt     480
gttttggcac caaaatcaac gggactttcc aaaatgtcgt aacaactccg ccccattgac     540
gcaaatgggc ggtaggcgtg tacggtggga ggtctatata agcagagctc gtttagtgaa     600
ccgtcagatc gcctggagac gccatccacg ctgttttgac ctccatagaa gacaccggga     660
ccgatccagc ctccgcggcc gggaacggtg cattggaacg cggattcccc gtgccaagag     720
tgacgtaagt accgcctata gagtctctag gcccaccccc ttggcttctt atgcatgcta     780
tactgttttt ggcttggggt ctatacaccc ccgcttcctc atgttatagg tgatggtata     840
gcttagccta taggtgtggg ttattgacca ttattgacca ctcccctatt ggtgacgata     900
ctttccatta ctaatccata acatggctct tgccacaac tctctttatt ggctatatgc     960
caatacactg tccttcagag actgacacgg actctgtatt tttacaggat ggggtctcat    1020
ttattattta caaattcaca tatacaacac caccgtcccc agtgcccgca gttttattta    1080
aacataacgt gggatctcca cgcgaatctc gggtacgtgt tccggaacgg tggagggcag    1140
tgtagtctga gcagtactcg ttgctgccgc gcgcgccacc agacataata gctgacagac    1200
taacagactg ttccttttcca tgggtattta aatctgcagt cttcgaacag gcgcgccgtg    1260
cgatccctgc ccggggtggca tccctgtgac ccctccccag tgcctctcct ggtcgtggaa    1320
ggtgctactc cagtgcccac cagccttgtc ctaataaaat taagttgcat cattttgttt    1380

-continued

```
gactaggtgt ccttgtataa tattatgggg tggaggcggg tggtatggag caaggggcag      1440
gttgggaaga caacctgtag ggccttcagg gtctattggg aaccaggctg gagtgcagtg      1500
gcacgatctt ggctcgctgc aatctccgcc tcctgggttc aagcgattct cctgcctcag      1560
tctcccgaat agttgggatt ccaggcatgc acgaccaggc tcagctaatt tttgtatttt      1620
tggtagagac ggggtttcac catattggcc agtctggtct ccatctcctg acctcaggta      1680
atccgcccgc ctcggcctcc caaattgctg ggattacagg tatgagccac tgggccttc       1740 cctgtcctgt gattttaaaa taattatacc agcagaagga cgtccagaca cagcatgggc      1800
tacctggcca tgcccagcca gttggacatt tgagttgttt gcttggcact gtcctctcat      1860
gaattcgata tccggaacgg tggagggcag tgtagtctga gcagtactcg ttgctgccgc      1920
gcgcgccacc agacataata gctgacagac taacagactg ttcctttcca tgggtctttt      1980
ctgcagtcac cgtccttgac acgggatccc tgcccgggtg catccctgt gacccctccc       2040 cagtgcctct cctggtcgtg aaggtgcta ctccagtgcc caccagcctt gtcctaataa       2100
aattaagttg catcattttg tttgactagg tgtccttgta taatattatg ggtggaggc       2160 gggtggtatg gagcaagggg caggttggga agacaacctg tagggccttc agggtctatt      2220
gggaaccagg ctggagtgca gtggcacgat cttggctcgc tgcaatctcc gcctcctggg      2280
ttcaagcgat tctcctgcct cagtctcccg aatagttggg attccaggca tgcacgacca      2340
ggctcagcta ttttttgtat ttttggtaga cggggtttt caccatattg gccagtctgg       2400
tctccatctc ctgacctcag gtaatccgcc cgcctcggcc tcccaaattg ctgggattac      2460
aggtatgagc cactgggccc ttccctgtcc tgtgattta aaataattat accagcagaa       2520
ggacgtccag acacagcatg gctacctgg ccatgcccag ccagttggac atttgagttg       2580
tttgcttggc actgtcctct catgaattcg tcgacagatc tgcgcagcac catggcctga     2640
aataacctct gaaagaggaa cttggttagg taccttctga ggcggaaaga accagctgtg      2700
gaatgtgtgt cagttagggt gtggaaagtc cccaggctcc ccagcaggca gaagtatgca     2760
aagcatgcat ctcaattagt cagcaaccag gtgtggaaag tccccaggct ccccagcagg     2820
cagaagtatg caaagcatgc atctcaatta gtcagcaacc atagtcccgc ccctaactcc     2880
gcccatcccg ccctaactc cgcccagttc cgcccattct ccgccccatg gctgactaat     2940 ttttttatt tatgcagagg ccgaggccgc ctcggcctct gagctattcc agaagtagtg      3000
aggaggcttt tttggaggcc taggcttttg caaaaagctt gattcttctg acacaacagt     3060
ctcgaactta agctgcagaa gttggtcgtg aggcactggg caggtaagta tcaaggttac     3120
aagacaggtt taaggagacc aatagaaact gggcttgtcg agacagagaa gactcttgcg     3180
tttctgatag gcacctattg gtcttactga catccacttt gcctttctct ccacaggtgt     3240
ccactcccag ttcaattaca gctcttaagg ctagagtact taatacgact cactataggc     3300
tagcatggtt cgaccattga actgcatcgt cgccgtgtcc caaaatatgg ggattggcaa     3360
gaacggagac ctaccctggc ctccgctcag gaacgagttc aagtacttcc aaagaatgac     3420
cacaacctct tcagtggaag gtaaacagaa tctggtgatt atgggtagga aaacctggtt     3480
ctccattcct gagaagaatc gacctttaaa ggacagaatt aatatagttc tcagtagaga     3540
actcaaagaa ccaccacgag gagctcattt tcttgccaaa agtttggatg atgccttaag     3600
acttattgaa caaccggaat tggcaagtaa agtagacatg gtttggatag tcggaggcag     3660
ttctgtttac caggaagcca tgaatcaacc aggccacctc agactctttg tgacaaggat     3720
```

-continued

```
catgcaggaa tttgaaagtg acacgttttt cccagaaatt gatttgggga aatataaact    3780
tctcccagaa tacccaggcg tcctctctga ggtccaggag gaaaaaggca tcaagtataa    3840
gtttgaagtc tacgaaaga aagactaact cgagaattca cgcgtggtac ctctagagtc    3900
gacccgggcg gccgcttcga gcagacatga taagatacat tgatgagttt ggacaaacca    3960
caactagaat gcagtgaaaa aaatgcttta tttgtgaaat tgtgatgct attgctttat     4020
ttgtaaccat tataagctgc aataaacaag ttaacaacaa caattgcatt cattttatgt    4080
ttcaggttca gggggaggtg tgggaggttt tttaaagcaa gtaaaacctc tacaaatgtg    4140
gtaaaatcga taaggatctg tcgacgaatt cactggccgt cgttttacaa cgtcgtgact    4200
gggaaaaccc tggcgttacc caacttaatc gccttgcagc acatccccct tcgccagct    4260
ggcgtaatag cgaagaggcc cgcaccgatc gcccttccca acagttgcgc agcctgaatg    4320
gcgaatggcg cctgatgcgg tattttctcc ttacgcatct gtgcggtatt cacaccgca     4380
tatggtgcac tctcagtaca atctgctctg atgccgcata gttaagccag ccccgacacc    4440
cgccaacacc cgctgacgcg ccctgacggg cttgtctgct cccggcatcc gcttacagac    4500
aagctgtgac cgtctccggg agctgcatgt gtcagaggtt ttcaccgtca tcaccgaaac    4560
gcgcgagacg aaagggcctc gtgatacgcc tatttttata ggttaatgtc atgataataa    4620
tggtttctta gacgtcaggt ggcacttttc ggggaaatgt gcgcggaacc cctatttgtt    4680
tatttttcta aatacattca aatatgtatc cgctcatgag acaataaccc tgataaatgc    4740
ttcaataata ttgaaaaagg aagagtatga gtattcaaca tttccgtgtc gcccttattc    4800
cctttttgc ggcattttgc cttcctgttt ttgctcaccc agaaacgctg gtgaaagtaa      4860
aagatgctga agatcagttg ggtgcacgag tgggttacat cgaactggat ctcaacagcg    4920
gtaagatcct tgagagtttt cgccccgaag aacgttttcc aatgatgagc acttttaaag    4980
ttctgctatg tggcgcggta ttatcccgta ttgacgccgg gcaagagcaa ctcggtcgcc    5040
gcatacacta ttctcagaat gacttggttg agtactcacc agtcacagaa aagcatctta    5100
cggatggcat gacagtaaga gaattatgca gtgctgccat aaccatgagt gataacactg    5160
cggccaactt acttctgaca acgatcggag gaccgaagga gctaaccgct tttttgcaca    5220
acatggggga tcatgtaact cgccttgatc gttgggaacc ggagctgaat gaagccatac    5280
caaacgacga gcgtgacacc acgatgcctg tagcaatggc aacaacgttg cgcaaactat    5340
taactggcga actacttact ctagcttccc ggcaacaatt aatagactgg atggaggcgg    5400
ataaagttgc aggaccactt ctgcgctcgg cccttccggc tggctggttt attgctgata    5460
aatctggagc cggtgagcgt gggtctcgcg gtatcattgc agcactgggg ccagatggta    5520
agccctcccg tatcgtagtt atctacacga cggggagtca ggcaactatg gatgaacgaa    5580
atagacagat cgctgagata ggtgcctcac tgattaagca ttggtaactg tcagaccaag    5640
tttactcata tactttag attgatttaa aacttcattt taatttaaa aggatctagg       5700
tgaagatcct tttgataat ctcatgacca aaatccctta acgtgagttt cgttccact      5760
gagcgtcaga ccccgtagaa aagatcaaag gatcttcttg agatcctttt tttctgcgcg    5820
taatctgctg cttgcaaaca aaaaaaccac cgctaccagc ggtggtttgt tgccggatc     5880
aagagctacc aactctttt ccgaaggtaa ctggcttcag cagagcgcag ataccaaata     5940
ctgtccttct agtgtagccg tagttaggcc accacttcaa gaactctgta gcaccgccta    6000
catacctcgc tctgctaatc ctgttaccag tggctgctgc cagtggcgat aagtcgtgtc    6060
ttaccgggtt ggactcaaga cgatagttac cggataaggc gcagcggtcg gctgaacgg     6120
```

```
ggggttcgtg cacacagccc agcttggagc gaacgaccta caccgaactg agatacctac    6180
agcgtgagct atgagaaagc gccacgcttc ccgaagggag aaaggcggac aggtatccgg    6240
taagcggcag ggtcggaaca ggagagcgca cgagggagct tccaggggga aacgcctggt    6300
atctttatag tcctgtcggg tttcgccacc tctgacttga gcgtcgattt ttgtgatgct    6360
cgtcaggggg gcggagccta tggaaaaacg ccagcaacgc ggccttttta cggttcctgg    6420
ccttttgctg gccttttgct cacatgttct ttcctgcgtt atcccctgat tctgtggata    6480
accgtattac cgcctttgag tgagctgata ccgctcgccg cagccgaacg accgagcgca    6540
gcgagtcagt gagcgaggaa gcggaagagc gcccaatacg caaaccgcct ctccccgcgc    6600
gttggccgat tcattaatgc agctggcacg acaggtttcc cgactggaaa gcgggcagtg    6660
agcgcaacgc aattaatgtg agttagctca ctcattaggc accccaggct ttacacttta    6720
tgcttccggc tcgtatgttg tgtggaattg tgagcggata caatttcac acaggaaaca    6780 gctatgacca tgattacgcc a                                              6801
```

<210> SEQ ID NO 30
<211> LENGTH: 9
<212> TYPE: RNA
<213> ORGANISM: Artificial Sequence
<220> FEATURE:
<223> OTHER INFORMATION: Splice site cassette
<220> FEATURE:
<221> NAME/KEY: misc_feature
<222> LOCATION: (1)..(1)
<223> OTHER INFORMATION: m is 'a' or 'c'
<220> FEATURE:
<221> NAME/KEY: misc_feature
<222> LOCATION: (6)..(6)
<223> OTHER INFORMATION: r is 'g' or 'a'

<400> SEQUENCE: 30 magguragu                                                               9

<210> SEQ ID NO 31
<211> LENGTH: 15
<212> TYPE: RNA
<213> ORGANISM: Artificial Sequence
<220> FEATURE:
<223> OTHER INFORMATION: Splice site cassette
<220> FEATURE:
<221> NAME/KEY: misc_feature
<222> LOCATION: (1)..(10)
<223> OTHER INFORMATION: y is 'c' or 't'
<220> FEATURE:
<221> NAME/KEY: misc_feature
<222> LOCATION: (11)..(11)
<223> OTHER INFORMATION: n is any nucleotide

<400> SEQUENCE: 31
yyyyyyyyyy ncagg                                                       15

<210> SEQ ID NO 32
<211> LENGTH: 20
<212> TYPE: DNA
<213> ORGANISM: Artificial Sequence
<220> FEATURE:
<223> OTHER INFORMATION: 5' light chain primer
<220> FEATURE:
<221> NAME/KEY: misc_feature
<222> LOCATION: (16)..(20)
<223> OTHER INFORMATION: n is any nucleotide

<400> SEQUENCE: 32

```
ttttggcgcg ccatgnnnnn                                                    20

<210> SEQ ID NO 33
<211> LENGTH: 20
<212> TYPE: DNA
<213> ORGANISM: Artificial Sequence
<220> FEATURE:
<223> OTHER INFORMATION: 5' heavy chain primer
<220> FEATURE:
<221> NAME/KEY: misc_feature
<222> LOCATION: (14)..(20)
<223> OTHER INFORMATION: n is any nucleotide

<400> SEQUENCE: 33
ttttggatcc atgnnnnnnn                                                    20

<210> SEQ ID NO 34
<211> LENGTH: 20
<212> TYPE: DNA
<213> ORGANISM: Artificial Sequence
<220> FEATURE:
<223> OTHER INFORMATION: 3' light chain primer
<220> FEATURE:
<221> NAME/KEY: misc_feature
<222> LOCATION: (16)..(20)
<223> OTHER INFORMATION: n is any nucleotide

<400> SEQUENCE: 34
gcacggcgcg ccctannnnn                                                    20

<210> SEQ ID NO 35
<211> LENGTH: 20
<212> TYPE: DNA
<213> ORGANISM: Artificial Sequence
<220> FEATURE:
<223> OTHER INFORMATION: 3' heavy chain primer
<220> FEATURE:
<221> NAME/KEY: misc_feature
<222> LOCATION: (14)..(20)
<223> OTHER INFORMATION: n is any nucleotide

<400> SEQUENCE: 35
gcagggatcc tcannnnnnn                                                    20
```